United States Patent
Isomura et al.

(10) Patent No.: US 8,567,231 B2
(45) Date of Patent: Oct. 29, 2013

(54) GAS SENSOR

(75) Inventors: Hiroshi Isomura, Nagoya (JP); Aya Sato, Komaki (JP); Takayoshi Atsumi, Konan (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 13/582,952

(22) PCT Filed: May 19, 2011

(86) PCT No.: PCT/JP2011/002795
§ 371 (c)(1),
(2), (4) Date: Sep. 5, 2012

(87) PCT Pub. No.: WO2011/148598
PCT Pub. Date: Dec. 1, 2011

(65) Prior Publication Data
US 2013/0000383 A1    Jan. 3, 2013

(30) Foreign Application Priority Data

May 24, 2010   (JP) ................................ 2010-118216

(51) Int. Cl.
*G01N 7/00* (2006.01)
(52) U.S. Cl.
USPC ......... 73/23.31; 73/31.05; 204/421; 204/424; 204/426; 204/431
(58) Field of Classification Search
USPC ................. 73/23.31, 31.05; 204/421–432
See application file for complete search history.

(56) References Cited

U.S. PATENT DOCUMENTS

| 6,096,372 | A  | * | 8/2000  | Nomura et al. | ............... 427/123 |
| 6,354,134 | B1 | * | 3/2002  | Katafuchi et al. | ............ 73/23.32 |
| 6,726,819 | B2 | * | 4/2004  | Atsumi et al. | ................ 204/428 |
| 7,032,433 | B2 |   | 4/2006  | Hayashi et al. | |
| 7,390,385 | B2 | * | 6/2008  | Ikoma et al. | .................. 204/428 |
| 7,413,641 | B2 | * | 8/2008  | Yamada et al. | ............... 204/428 |
| 2001/0054552 | A1 | * | 12/2001 | Matsuo et al. | ............... 204/421 |
| 2004/0144645 | A1 | * | 7/2004  | Yamada et al. | ............... 204/424 |
| 2005/0016849 | A1 | * | 1/2005  | Ikoma et al. | .................. 204/429 |

FOREIGN PATENT DOCUMENTS

| JP | 10-206378    | A | 8/1998  |
| JP | 2002-168830  | A | 6/2002  |
| JP | 2004-53425   | A | 2/2004  |
| JP | 2006-145369  | A | 6/2006  |
| JP | 2007-248123  | A | 9/2007  |
| JP | 2008-281584  | A | 11/2008 |

* cited by examiner

*Primary Examiner* — Hezron E Williams
*Assistant Examiner* — Hoang Nguyen
(74) *Attorney, Agent, or Firm* — Sughrue Mion, PLLC

(57) ABSTRACT

A gas sensor includes an inner electrode formed on an inner surface of a base body. The inner electrode has an inner sensing portion formed in a gas contact inner region such that the inner sensing portion is located on the whole of a heat-facing area of the gas contact inner region facing a heating portion in a radial direction of the base body, a terminal contact portion formed in a rear end region such that the terminal contact portion is located in at least a part of the rear end region in a circumferential direction of the base body and a lead portion formed only on a part of the inner surface of the base body in the circumferential direction of the base body so as to connect the inner sensing portion and the terminal contact portion to each other.

8 Claims, 24 Drawing Sheets

GAS SENSOR

CROSS REFERENCE TO RELATED APPLICATIONS

This application is a National Stage of International Application No. PCT/JP2011/002795, filed on May 19, 2011, which claims priority from Japanese Patent Application No. 2010-118216, filed on May 24, 2010, the contents of all of which are incorporated herein by reference in their entirety.

TECHNICAL FIELD

The present invention relates to a gas sensor.

BACKGROUND ART

There is known a gas sensor of the type mounted on an exhaust pipe of an automotive vehicle so as to detect the concentration of oxygen in exhaust gas. This gas sensor includes a gas sensor element having a bottomed cylindrical base body formed of a solid electrolyte with a closed front end and an open rear end and extending in an axial direction of the gas sensor, an outer electrode formed of noble metal (such as platinum) on an outer surface of the base body and an inner electrode formed of noble metal (such as platinum) on an inner surface of the base body (see, for example, Patent Document 1).

PRIOR ART DOCUMENTS

Patent Documents

Patent Document 1: Japanese Laid-Open Patent Publication No. 2007-248123

In the Patent Document 1, the following method is disclosed for forming the electrode of noble metal (platinum) on the inner surface of the base body. A nucleus application step is first performed to apply nuclei onto the inner surface of the base body. More specifically, an aqueous platinic chloride solution (platinum concentration: 0.5 g/L) is filled into the inside of the base body, heated, and then, discharged from the inside of the base body, thereby forming a coating of the aqueous platinic chloride solution on the whole of the inner surface of the base body. An aqueous hydrazine solution (concentration: 5 mass %) is subsequently filled into the inside of the base body, heated at 75° C. and left for 30 minute. As a result, platinum nuclei are deposited on the whole of the inner surface of the base body. A plating step is next performed by mixing an aqueous platinum complex salt solution (platinum concentration: 15 g/L) with an aqueous hydrazine solution (concentration: 85 mass %), filling the resulting plating liquid into the inside of the base body, heating the plating liquid and thereby depositing platinum out of the plating liquid. In this way, the electrode of noble metal (platinum) is formed on the whole of the inner surface of the base body in the gas sensor of Patent Document 1.

DISCLOSURE OF THE INVENTION

Problems to be Solved by the Invention

In view of the fact that noble metal such as platinum is expensive and rare, there has recently been a demand to minimize the amount of noble metal used.

Further, the gas sensor cannot obtain a stable sensor output until the solid electrolyte base body reaches a predetermined activation temperature. The gas sensor of Patent Document 1 thus has a heater (heating portion) arranged in a cylindrical inner space of the base body so as to heat the base body for the purpose of rapidly raising the temperature of the solid electrolyte base body to the activation temperature. As mentioned above, there has also been a demand that the gas sensor can obtain a stable sensor output quickly by energization of the heater.

The present invention has been made in view of the above circumstances. It is an object of the present invention to provide a gas sensor capable of obtaining a stable sensor output quickly by energization of a heater while reducing the amount of noble metal used on the inner surface of a base body.

Means for Solving the Problems

According to one aspect of the present invention, there is provided a gas sensor, comprising: a gas sensor element for detecting a specific gas component in gas under measurement, the gas sensor element including: a bottomed cylindrical base body formed of a solid electrolyte with a closed front end and an open rear end and extending in an axial direction of the gas sensor; an outer electrode formed of noble metal on an outer surface of the base body; and an inner electrode formed of noble metal on an inner surface of the base body; and a heater having a heating portion arranged in a cylindrical inner space of the base body, wherein the outer surface of the base body includes a gas contact region located on a front end side of the base body such that the gas under measurement comes into contact with the gas contact region; wherein the inner surface of the base body includes a gas contact inner region located at a position inside of the gas contact region in a thickness direction of the base body and a rear end region spaced apart from the gas contact inner region in the axial direction and located at a rear end side of the base body; wherein the heating portion has a heating resistor pattern located only in the same axial range as that of the gas contact inner region in the axial direction; wherein the inner electrode has: an inner sensing portion formed only in the gas contact inner region such that the inner sensing portion is located on at least the whole of a heat-facing area of the gas contact inner region that faces the heating resistor pattern of the heating portion in a radial direction of the base body; a terminal contact portion formed in the rear end region such that the terminal contact portion is located on at least a part of the rear end region in a circumferential direction of the base body; and a lead portion formed only on a part of the inner surface in the circumferential direction of the base body so as to connect the inner sensing portion and the terminal contact portion to each other; and wherein the outer electrode has an outer sensing portion formed in the gas contact region such that a part of the outer sensing portion is located on at least an area of the gas contact region inside of which the inner sensing portion is located in the thickness direction of the base body.

It is preferable in the above gas sensor that the inner sensing portion is formed only on the heat-facing area.

It is preferable in the above gas sensor that the inner sensing portion is formed only on a part of the gas contact inner region in the circumferential direction of the base body.

It is preferable in the above gas sensor that the lead portion extends linearly in the axial direction.

It is preferable in the above gas sensor that the heater is in contact with the inner sensing portion.

It is preferable in the above gas sensor that a rear end of the inner sensing portion is located rear of a rear end of the outer sensing portion.

It is preferable to, when the rear end of the inner sensing portion is located rear of the rear end of the outer sensing portion, satisfy the condition: $1.1 \leq T1/T2$ where T1 is a length between a front end of the gas sensor element and the rear end of the inner sensing portion in the axial direction; and T2 is a length between the front end of the gas sensor element and the rear end of the outer sensing portion in the axial direction.

It is preferable in the above gas sensor that a thickness of the outer sensing portion is larger than a thickness of the inner sensing portion.

It is preferable in the above gas sensor that the heat-facing area is located on the inner surface of a part of the base body having a thickness of d to 2d where d is a minimum thickness of the base body.

Further, it is preferable in the above gas sensor that the heat-facing area is located on the inner surface of a part of the base body that reaches 70% or higher of a maximum heating temperature of the gas sensor element.

Effects of the Invention

In the gas sensor of claim 1, the heating resistor pattern of the heating portion is located within the same axial range as that of the gas contact inner region in the axial direction. It means that the heating resistor pattern of the heating portion has a rear end (rearmost end) located front of a rear end of the gas contact inner region (located nearer to a front end of the base body) and a front end (frontmost end) located rear of a front end of the gas contact inner region (located nearer to a rear end of the base body) in the axial direction of the base body. Namely, the whole of the heating portion of the heater is located at a position facing the gas contact inner region in the radial direction (the direction of cylinder diameter) of the base body. The heating resistor pattern of the heating portion is formed by e.g. shaping a linear heating resistor into a predetermined pattern (such as a zigzag pattern or a spiral pattern) so as to generate heat upon energization thereof.

Further, the inner sensing portion of the inner electrode is formed only in the gas contact inner region; the terminal contact portion of the inner electrode is formed in the rear end region; and the lead portion of the inner electrode is formed so as to connect the inner sensing portion and the terminal contact portion to each other in the above gas sensor. In particular, the lead portion is formed only on the part of the inner surface of the base body in the circumferential direction of the base body. It is possible to reduce the amount of noble metal used on the inner surface of the base body by forming the lead portion only on the part of the inner surface in the circumferential direction of the base body (e.g. forming the lead portion in a linear shape) rather than forming the lead portion on the whole (entire circumference) of the inner surface in the circumferential direction of the base body (forming the lead portion in a cylindrical shape).

Furthermore, the inner sensing portion is located on at least the whole of the heat-facing area of the gas contact inner region that faces the heating portion in the radial direction of the base body; and the outer sensing portion is formed such that the part of the outer sensing portion is located on at least the area of the gas contact region inside of which the inner sensing portion is located in the thickness direction of the base body. It is possible to obtain a stable sensor output quickly upon energization of the heater by forming the inner sensing portion on at least the whole of the heat-facing area.

More specifically, the above gas sensor cannot obtain a stable sensor output until the solid electrolyte base body (the solid electrolyte body containing e.g. zirconia as a main component) reaches a predetermined activation temperature. The solid electrolyte base body is thus heated by the heater (heating portion) for the purpose of rapidly raising the temperature of the base body to the activation temperature. As is apparent, the part of the base body facing the heating portion in the radial direction (corresponding to the region of the inner surface including the heat-facing area) is easiest to heat and can be activated most rapidly upon energization of the heater. It is possible to obtain a stable sensor output quickly upon energization of the heater by forming the inner sensing portion on at least the whole of the heat-facing area and by forming the part of the outer sensing portion on the area inside of which the inner sensing portion is located.

In the gas sensor of claim 2, the inner sensing portion of noble metal is formed only on the heat-facing area. It is thus possible to further reduce the amount of noble metal used in the gas sensor as compared to the case of forming the inner sensing portion on not only the heat-facing area but also any other area of the gas contact inner region (e.g. forming the inner sensing portion on the whole of the gas contact inner region). It is also possible to obtain a stable sensor output quickly upon energization of the heater by forming the inner sensing portion only on the heat-facing area.

In the gas sensor of claim 3, the inner sensing portion of noble metal is formed only on the part of the gas contact inner region in the circumferential direction of the base body. It is thus possible to further reduce the amount of noble metal used in the gas sensor as compared to the case of forming the inner sensing portion on the gas contact inner region throughout the circumferential direction of the base body.

Preferably, the heater is in contact with the inner sensing portion in the above gas sensor. When the inner sensing portion is formed only on the part of the gas contact inner region in the circumferential direction of the base body and selectively brought into contact with the heater, the part of the base body on which the inner sensing portion is formed is easier to heat and can be activated more rapidly. It is thus possible to obtain a stable sensor output more quickly upon energization of the heater.

In the gas sensor of claim 4, the lead portion is in the form of extending linearly in the axial direction such that the amount of the noble metal used in the lead portion can be limited to a very small level. It is thus possible to further reduce the amount of noble metal used in the gas sensor.

In the gas sensor of claim 5, the heater is in contact with the inner sensing portion so that the part of the base body on which the inner sensing portion is formed is easier to heat and can be activated more rapidly. The gas sensor can thus obtain a stable sensor output more quickly.

It is particularly effective to bring the heater into contact with the inner sensing portion in the gas sensor where the inner sensing portion is formed only on the part of the gas contact inner region in the circumferential direction of the base body. This is because, when the inner sensing portion is formed only on the part of the gas contact inner region in the circumferential direction of the base body and selectively brought into contact with the heater, the part of the base body on which the inner sensing portion is formed is easier to heat and can be activated more rapidly. It is thus possible to obtain a more stable sensor output more quickly upon energization of the heater.

Not only in the case where the inner sensing portion is formed at a position closer to the heater than the outer sensing portion but also in the case where the inner sensing portion is formed on the whole of the heat-facing area or brought into contact with the heater, it becomes easier to heat the inner sensing portion so that the inner sensing portion may deteriorate earlier than the outer sensing portion. In the gas sensor of claim 6, the inner sensing portion is formed so as to reach a rear side of the outer sensing portion. It is thus possible to increase the surface area of the inner sensing portion and prevent the inner sensing portion from deteriorating earlier than the outer sensing portion.

In the gas sensor of claim 7, when the rear end of the inner sensing portion is located rear of the rear end of the outer sensing portion, the condition: $1.1 \leq T1/T2$ is satisfied where T1 is the length between the front end of the gas sensor element and the rear end of the inner sensing portion in the axial direction; and T2 is the length between the front end of the gas sensor element and the rear end of the outer sensing portion in the axial direction. It is thus possible to further increase the surface area of the inner sensing portion and more effectively prevent the inner sensing portion from deteriorating earlier than the outer sensing portion. The above effect may not be obtained when the length T1 and the length T2 satisfy the condition: $1.1 > T1/T2 > 1.0$. When the length T1 and the length T2 satisfy the condition: $3 \leq T1/T2$, the amount of noble metal used becomes increased due to too large surface area of the inner sensing portion 21g. For this reason, it is particularly preferable to satisfy the condition: $T1/T2 < 3$.

In the gas sensor of claim 8, the thickness of the outer sensing portion is larger than the thickness of the inner sensing portion. As the outer sensing portion is directly exposed to the gas under measurement, the outer sensing portion is more susceptible to deterioration by poisoning substances and the like than the inner sensing portion. It is possible to prevent the outer sensing portion from deteriorating earlier than the inner sensing portion by setting the thickness of the outer sensing portion to be larger than the thickness of the inner sensing portion.

In the gas sensor of claim 9, the part of the base body having a thickness of d to 2d can be rapidly heated to the activation temperature because of its small volume of solid electrolyte. It is possible to quickly obtain a stable sensor output by forming the heat-facing area on this part of the base body.

In the gas sensor of claim 10, the part of the solid electrolyte base body that reaches 70% or higher of the maximum heating temperature of the gas sensor element can be rapidly heated to an activation temperature. It is possible to quickly obtain a stable sensor output by forming the heat-facing area on this part of the base body.

BEST MODES FOR CARRYING OUT THE INVENTION

[First Embodiment]

A first embodiment of the present invention will be described below with reference to the drawings.

Figure 1:
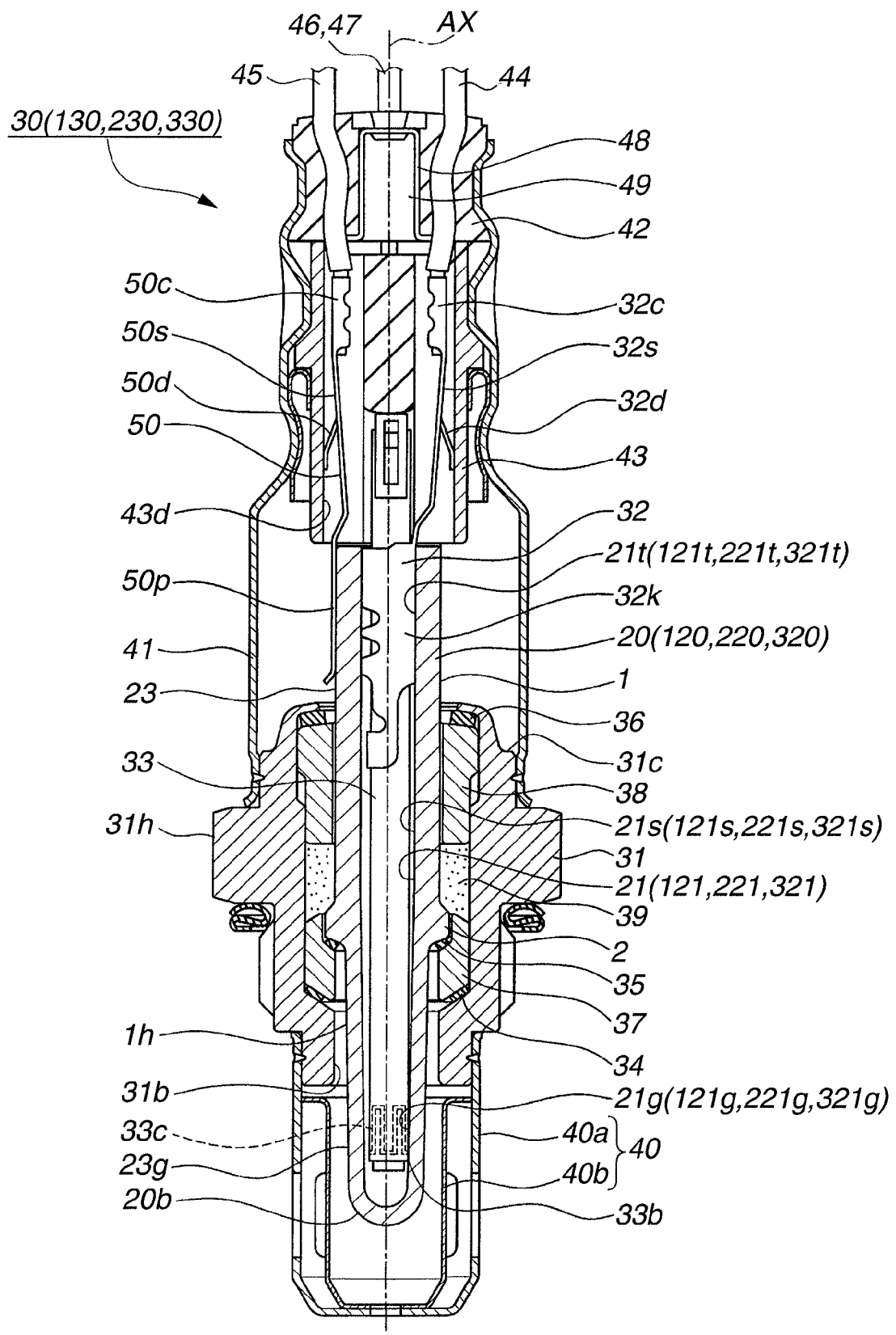
FIG. 1 is a vertical cross-section view of a gas sensor according to first to fourth embodiments of the present invention.

As shown in FIG. 1, a gas sensor 30 of the first embodiment includes a gas sensor element 20 having a base body 1 and a cylindrical metal shell 31 surrounding the gas sensor element 20. The gas sensor 30 further includes an outer terminal member 50, an inner terminal member 32 and a heater 33.

The heater 33 has a cylindrical column shape extending in an axial direction of the gas sensor 30 (the direction of an axis AX; vertical direction in FIG. 1) and includes a heating portion 33c on a front end side thereof. The heating portion 33c is formed by shaping a linear heating resistor into a predetermined pattern (e.g. zigzag pattern) so as to generate heat upon energization thereof and is arranged on an outer circumferential surface of the heater 33 throughout a circumferential direction of the heater 33. The heater 33 (heating portion 33c) is located inside the gas sensor element 20 (in a cylindrical inner space of the base body 1) and held in position by the inner terminal member 32. More specifically, the heater 33 is held by the inner terminal member 32 in such a manner that a front end portion 33b of the heater 33 is kept in contact with an inner electrode 21 (inner sensing portion 21g) of the gas sensor element 20 in the first embodiment.

The metal shell 31 retains, in a hollow cylindrical inner space thereof, a flange portion 2 of the gas sensor element 20 (base body 1) with metal packings 34, 35 and 36, insulators 37 and 38 and talc powder 39 disposed between the metal shell 31 and the gas sensor element 20. With this, the gas sensor element 20 is held by the metal shell 31 in such a manner that a front end portion 20b of the gas sensor element 20 protrudes from an front end opening 31b of the metal shell 31.

A protector 40 is attached to the metal shell 31 so as to cover therewith the front end portion 20b of the gas sensor element 20 protruding from the front end opening 31b of the metal shell 31. The protector 40 has a double structure consisting of an outer protector member 40a and an inner protector member 40b. A plurality of gas holes are formed in the outer protector member 40a and the inner protector member 40b for passage of exhaust gas. The exhaust gas is thus introduced through the gas holes of the protector 40 and brought into contact with an outer sensing portion 23g of an outer electrode 23 on an outer surface 1h of the base body 1. In the first embodiment, the packings 34 and 35 establish sealing in the gas sensor 30 such that the exhaust gas introduced to the inside of the gas sensor 30 through the gas holes of the protector 40 does not flow into the rear side (top side in FIG. 1) of the flange portion 2 of the gas sensor element 20.

The gas sensor element 20 of the first embodiment will be explained below in detail. The gas sensor element 20 includes the base body 1 formed into a bottomed cylindrical shape, the outer electrode 23 formed of noble metal (more specifically, platinum) on the outer surface 1h of the base body 1 and the inner electrode 21 formed of noble metal (more specifically, platinum) (as a noble metal plating layer) on an inner surface 1k of the base body 1 (see FIGS. 5 to 7). This gas sensor element 20 is adapted to detect a specific gas component (oxygen component) in the gas under measurement (exhaust gas).

Figure 5:
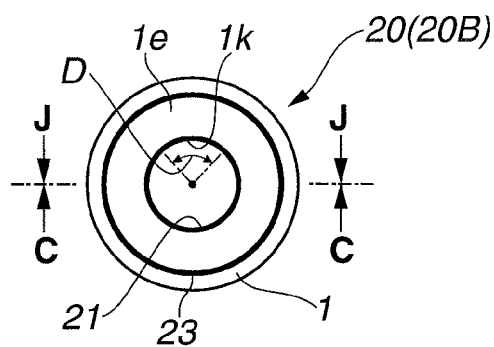
FIG. 5 is a top view of a gas sensor element according to the first embodiment of the present invention.
Figure 6:
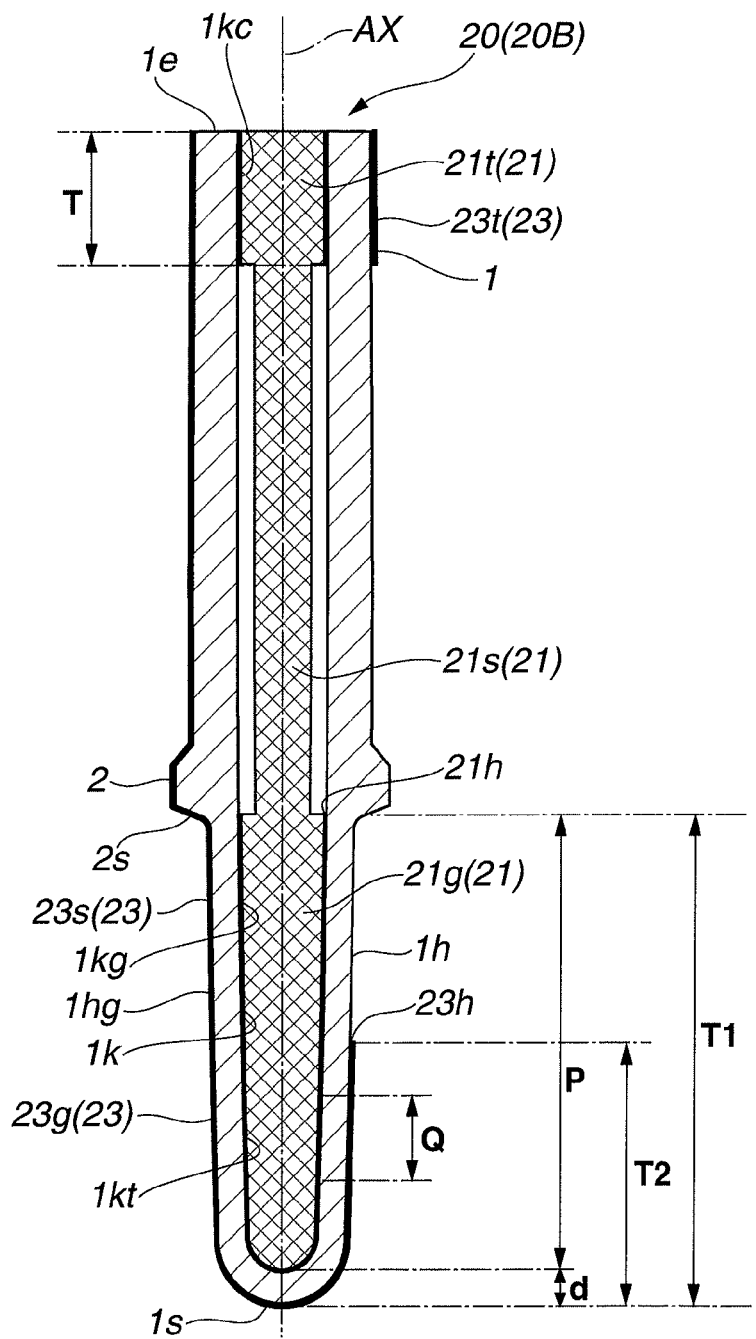
FIG. 6 is a vertical cross-section view of the gas sensor element taken along arrows C-C in FIG. 5.
Figure 7:
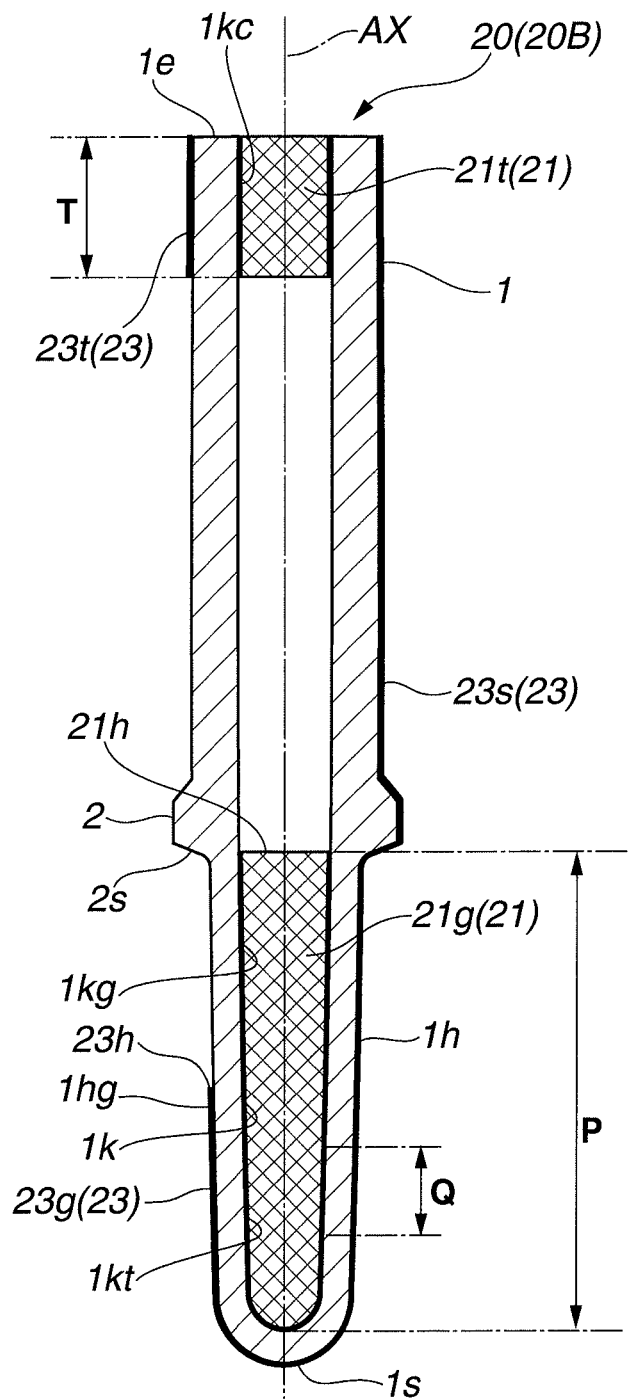
FIG. 7 is a vertical cross-section view of the gas sensor element taken along arrows J-J in FIG. 5.

It is noted that: FIG. 5 is a top view of the gas sensor element 20 (i.e. a view of the gas sensor element 20 as viewed from the side of a rear end 1e of the base body 1 in the direction of the axis AX); FIG. 6 is a cross-section view of the gas sensor element 20 taken along arrows C-C in FIG. 5; and FIG. 7 is a cross-section view of the gas sensor element 20 taken along arrows J-J in FIG. 5.

Figure 2:
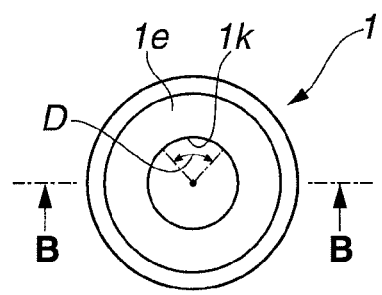
FIG. 2 is a top view of a base body according to the first to fourth embodiment of the present invention.
Figure 3:
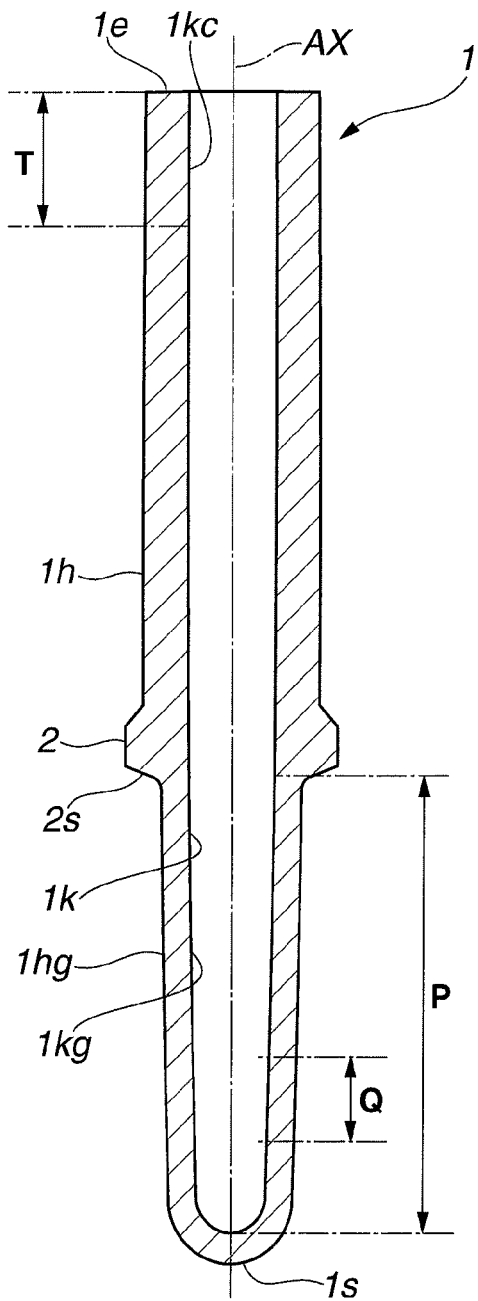
FIG. 3 is a vertical cross-section view of the base body taken along arrows B-B in FIG. 2.

The base body 1 is formed of a solid electrolyte containing zirconia as a main component and has the bottomed cylindrical shape extending in the axial direction (the direction of the axis AZ; vertical direction in FIG. 3) with a front end 1s (bottom side in FIG. 3) thereof closed and a rear end 1e (top side in FIG. 3) thereof opened (see FIGS. 2 and 3). The flange portion 2 is formed into an annular, radially outwardly protruding shape at a substantially middle position of the base body 1 in the axial direction (the direction of the axis AZ; vertical direction in FIG. 3).

It is noted that: FIG. 2 is a top view of the base body 1 (i.e. a view of the base body 1 as viewed from the side of the rear end 1e of the base body 1); and FIG. 3 is a cross-section view of the base body 1 taken along arrows B-B in FIG. 2.

The base body 1 can be formed by e.g. molding a zirconia-based solid electrolyte material into a bottomed cylindrical compact by a known press-forming process and firing the molded compact at 1500° C. for about 2 hours.

The outer surface 1h of the base body 1 includes a gas contact region 1hg located on a side thereof closer to the front end 1s of the base body 1 such that the gas under measurement comes into contact with the gas contact region 1hg (see FIG. 3). The gas contact region 1hg corresponds to the whole of a part of the outer surface 1h of the base body 1 located closer to the front end is than a front end part 2s (bottom side in FIG. 3) of the flange portion 2.

The inner surface 1k of the base body 1 includes a gas contact inner region 1kg located at a position inside of the gas contact region 1hg of the outer surface 1h in a thickness direction of the base body 1. The gas contact inner region 1kg corresponds to the whole of a part of the inner surface 1k located within an axial range P as shown in FIG. 3. The inner surface 1k further includes a rear end region 1kc spaced apart from the gas contact inner region 1kg in the axial direction (the direction of the axis AX; vertical direction in FIG. 3) and located on a side thereof closer to the rear end 1e of the base body 1. As shown in FIG. 3, the rear end region 1kc corresponds to the whole of a part of the inner surface 1k located within an axial range T.

Figure 4:
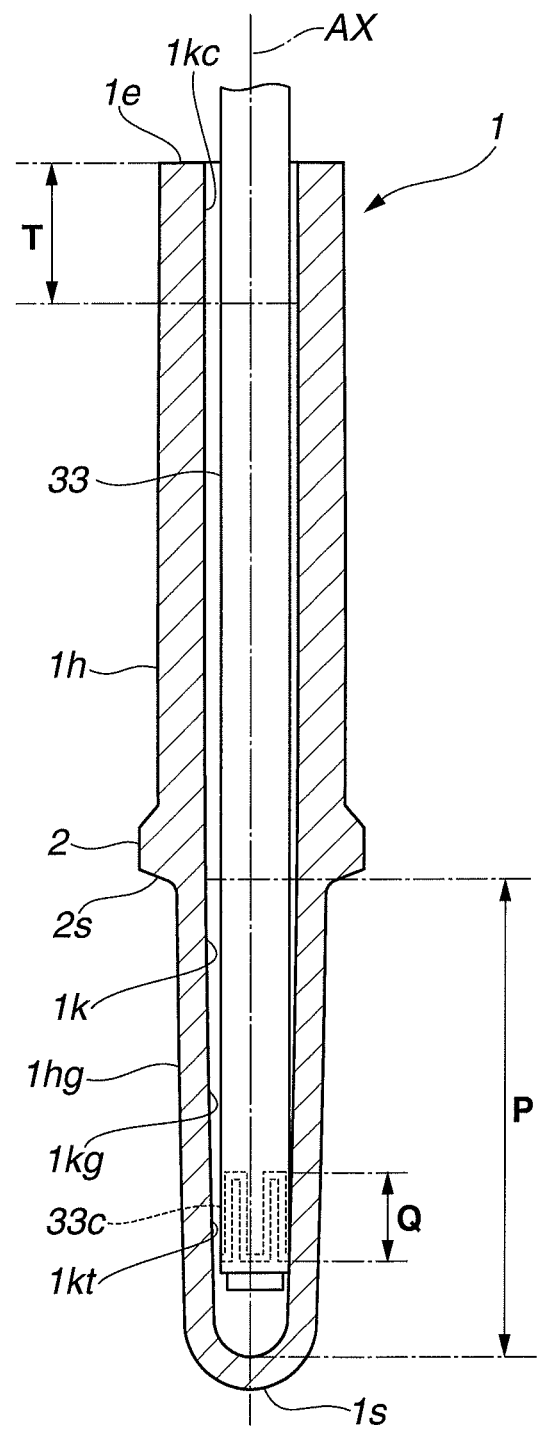
FIG. 4 is a schematic view showing a positional relationship of the base body with a heater (heating portion) in the gas sensor.

In the gas sensor 30 of the first embodiment, the heating resistor pattern of the heating portion 33c of the heater 33 is arranged within the same axial range as that of the gas contact inner region 1kg in the axial direction (the direction of the axis AX) (i.e. within the axial range P). Hereinafter, an area of the gas contact inner region 1kg facing the heating resistor pattern of the heating portion 33c in a radial direction of the base body 1 (a direction perpendicular to the axis AX) (corresponding to the whole of the area of the gas contact inner region 1kg located within the axial range Q) is referred to as "heat-facing area 1kt". It is noted that FIG. 4 is a schematic view showing the positional relationship of the base body 1 and the heater 33 (heating portion 33c) in the first to fourth embodiments.

As shown in FIGS. 6 and 7, the inner electrode 21 has the inner sensing portion 21g formed only in the gas contact inner region 1kg, an inner contact portion 21t formed in the rear end region 1kc and an inner lead portion 21s connecting the inner sensing portion 21g and the inner contact portion 21t to each other.

The inner sensing portion 21g is located on at least the whole of the heat-facing area 1kt of the gas contact inner region 1kg. More specifically, the inner sensing portion 21g is located on the whole of the gas contact inner region 1kg including the heat-facing area 1kt (i.e. on the whole of a part of the inner surface 1k extending from the front end of the base body 1 to the front end part 2s of the flange portion 2) in the first embodiment. The inner contact portion 21t is located on at least a part of the rear end region 1kc in the circumferential direction of the base body 1 (the circumferential direction along the inner surface 1k in FIG. 2). More specifically, the inner contact portion 21t is located on the rear end region 1kc throughout the circumferential direction of the base body 1 (the entire circumference of the rear end region 1 kc) in the first embodiment.

Further, the inner lead portion 21s is formed only on a part of the inner surface 1k in the circumferential direction of the base body 1. More specifically, the inner lead portion 21 is formed only on a circumferential range D (a range of circular arc having a central angle of 80°, see FIG. 5) of the inner surface 1k in such a manner as to extend linearly in the axial direction (the direction of the axis AX) (see FIGS. 5 to 7).

As described above, it is possible to reduce the amount of the noble metal (in the first embodiment, platinum) used on the inner surface 1k of the base body 1 by forming the inner lead portion 21s only on the part of the inner surface 1k in the circumferential direction of the base body 1 rather than by forming the inner lead portion 21s on the whole (entire circumference) of the inner surface 1k in the circumferential direction of the base body 1. In particular, the lead portion 21s is in the form of extending linearly in the axial direction such that the amount of the noble metal used in the inner lead portion 21s can be limited to a very small level. This allows a further reduction of the amount of the noble metal used in the gas sensor 30 of the first embodiment.

The outer electrode 23 has the outer sensing portion 23g formed in the gas contact region 1hg (see FIGS. 6 and 7). A part of the outer sensing portion 23g is located on at least an area of the gas contact region 1hg inside of which the inner sensing portion 21g is located in the thickness direction of the base body 1. More specifically, the outer sensing portion 23g is located on the whole of a substantially half part of the gas contact region 1hg in the axial direction (i.e. on the whole of a part of the outer surface 1h extending from the front end of the base body 1 to a point located closer to the rear end 1e than a part of the outer surface 1h facing the heat-facing area 1kt and closer to the front end 1s than the front end part 2s of the flange portion 2) (see FIG. 6). The outer electrode 23 also has an outer lead portion 23s and an outer contact portion 23t formed on the outer surface of the base body 1 such that the outer lead portion 23s connects to the outer sensing portion 23g and extends linearly in the axial direction and such that the outer contact portion 23t connects to the outer lead portion 23s.

As mentioned above, the inner sensing portion 21g is formed on at least the whole of the heat-facing area 1kt of the gas contact inner region 1kg in the gas sensor 30 of the first embodiment. This makes it possible to obtain a stable sensor output quickly upon energization of the heater 33 (heating portion 33c) as mentioned below.

In more detail, the gas sensor 30 of the first embodiment cannot obtain a stable sensor output until the solid electrolyte base body 1 (the solid electrolyte body containing zirconia as the main component) reaches a predetermined activation temperature. The base body 1 is thus heated by the heater 33 (heating portion 33c) for the purpose of rapidly raising the temperature of the solid electrolyte base body 1 to the activation temperature in the gas sensor 30 of the first embodiment.

Figure 8:
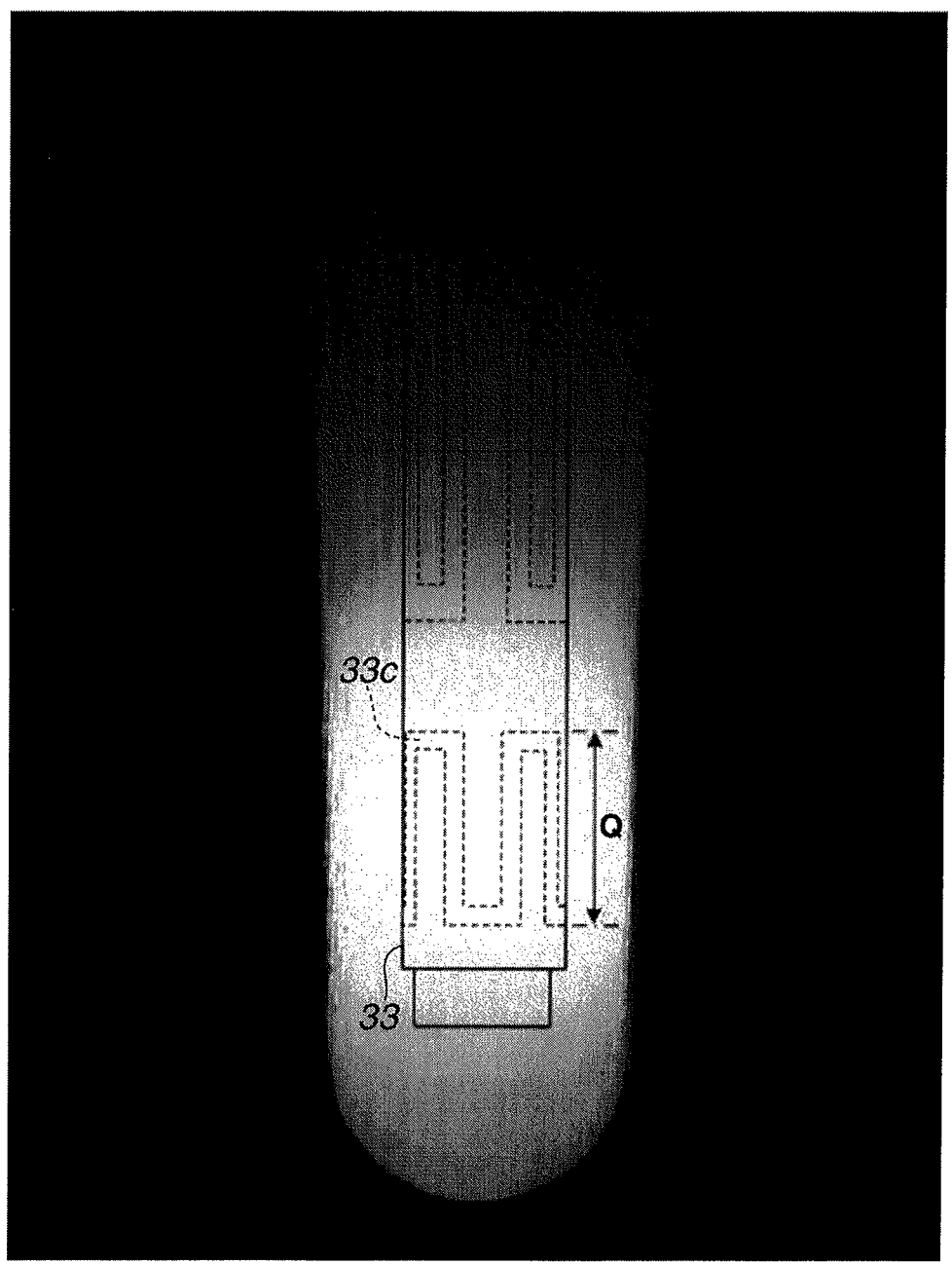
FIG. 8 is a thermography image of the gas sensor element in a state that the gas sensor element is heated by the heater.

It is noted that FIG. 8 is a thermography image of the gas sensor element 20 (base body 1) in a state that the gas sensor element 20 (base body 1) is heated by energization of the heater 33 (heating portion 33c) (after the lapse of a predetermined time from the initiation of the energization) in the gas sensor 30 of the first embodiment. In the thermography image of FIG. 8, the high-temperature part is indicated in light color (white); and the low-temperature part is indicated in dark color (black). The image of FIG. 8 is herein taken in the direction perpendicular to the axis AX (the radial direction) from the side on which the gas sensor element 20 (base body 1) is in contact with the front end portion 33b (right side in FIGS. 1 and 4) of the heater 33.

Further, the heater 33 (heating portion 33c) is illustrated as a reference in FIG. 8 in order to indicate the positional relationship of the gas sensor element 20 (base body 1) and the heater 33 (heating portion 33c). The range where the heating portion 33c is located in the axial direction (vertical direction in FIG. 8) is referred to as "axial range Q". The bottom side in FIG. 8 corresponds to the side closer to the front end 1s of the base body 1.

In the thermography image of FIG. 8, the part of the base body 1 facing the heating portion 33c in the radial direction (i.e. the part of the base body 1 located within the axial range Q, corresponding to the region of the inner surface 1k including the heat-facing area 1kt) is indicated in the lightest color. This part reaches a temperature higher than or equal to 70% of the maximum heating temperature of the gas sensor element 20. It is thus apparent that the part of the base body 1 facing the heating portion 33c in the radial direction is easiest to heat and can be activated most rapidly upon energization of the heater 33. Accordingly, the gas sensor 30 of the first embodiment is so configured that: the inner sensing portion 21g is formed on at least the whole of the heat-facing area 1kt; and the part of the outer sensing portion 23g is formed on the area inside of which the inner sensing portion 21g is located. It is thus possible that the gas sensor 30 can obtain a stable sensor output quickly by energization of the heater 33.

Further, the gas sensor 30 of the first embodiment is so configured that a rear end 21h of the inner sensing portion 21g is located rear of a rear end 23h of the outer sensing portion 23g. It becomes easier to heat the inner sensing portion 21g so that the inner sensing portion 21g may deteriorate earlier than the outer sensing portion 23g not only in the case where the inner sensing portion 21g is formed at a position closer to the heater 33 than the outer sensing portion 23g but also in the case where the inner sensing portion 21g is formed on the whole of the heat-facing area 1kt or brought into contact with the heater 33. It is however possible to increase the surface area of the inner sensing portion 21g and prevent the inner sensing portion 21g from deteriorating earlier than the outer sensing portion 23g by forming the inner sensing portion 21g so as to reach a rear side of the outer sensing portion 23g.

When the rear end 21h of the inner sensing portion 21g is located rear of the rear end 23h of the outer sensing portion 23g, the condition: T1/T2=2.1 is set where T1 is a length between the front end 1s of the gas sensor element 20 and the rear end 21h of the inner sensing portion 21g in the axial direction; and T2 is a length between the front end 1s of the gas sensor element 1 and the rear end 23h of the outer sensing portion 23g. It is possible by satisfaction of the condition: 1.1<T1/T2 to further increase the surface area of the inner sensing portion 21g and more effectively prevent the inner sensing portion 21g from deteriorating earlier than the outer sensing portion 23g.

Furthermore, the inner sensing portion 21g has a thickness of 1 μm; and the outer sensing portion 23g has a thickness of 1.3 μm. That is, the thickness of the outer sensing portion 23g is larger than the thickness of the inner sensing portion 21g in the gas sensor 30 of the first embodiment. It is thus possible to prevent the outer sensing portion 23g from deteriorating earlier than the inner sensing portion 21g even when the outer sensing portion 23g is directly exposed to the gas under measurement and subjected to deterioration by poisoning substances.

In the gas sensor 30 of the first embodiment 1, the heat-facing area 1kt is formed on the inner surface 1k of a part of the base body 1 having a thickness of d to 2d where d is the minimum thickness of the base body 1. In the first embodiment, the front end 1s of the base body has the minimum thickness d; and the whole of the part of the base body 1 located closer to the front end 1s than the front end part 2s of the flange portion 2 has a thickness of d to 2d. The part of the base body 1 having such a thickness of d to 2d can be rapidly heated to the activation temperature because of its small volume of solid electrolyte. It is thus possible to quickly obtain a stable sensor output by forming the heat-facing area $1kt$ on this part.

In order to obtain a stable sensor output, it is preferable that 40% or more of the surface area of the inner sensing portion $21g$ faces the outer sensing portion $23g$. If the percentage of the surface area of the inner sensing portion $21g$ facing the outer sensing portion $23g$ is less than 40%, the gas sensor may not obtain a stable sensor output. In addition, the amount of the noble metal used in the inner and outer sensing portions $21g$ and $23g$ becomes increased.

A cylindrical outer metal tube 41 is fixed to the metal shell 31 by laser welding, from outside, the entire circumference of a font end portion of the outer metal tube 41 to the contact portion $31c$ on a rear end side (top side in FIG. 1) of the metal shell 31 in the gas sensor 30 of the first embodiment. A rear end opening of the outer metal tube 41 is sealed by crimping with a grommet 42 of fluoro rubber fitted therein. A separator 43 of insulating alumina ceramic material is disposed on a front end side (bottom side in FIG. 1) of the grommet 42. Further, sensor output leads 44 and 45 and heater leads 46 and 47 are inserted in through holes of the grommet 42 and in a through hole 43 (retaining hole $43d$) of the separator 43. The heater leads 46 and 47 are connected to external terminals of the heater 33.

A through hole is formed in the center of the grommet 42 along the axis AX.

In this through hole, a metallic pipe 49 covered with a sheet-shaped filter 48, which combines water repellency with air permeability, is fitted. The air outside the gas sensor 30 is thus introduced into the outer metal tube 41 through the filter 48 and then into the gas sensor element 20 and brought into contact with the inner sensing portion $21g$ of the inner electrode 21.

The outer terminal member 50 is formed of a stainless steel plate and includes a outer engagement portion $50p$ having a substantially C-shaped cross section in the direction of the axis AX, a separator insertion portion $50s$ extending toward the rear from the center of a rear end side of the outer engagement portion $50p$ and a connector portion $50c$ located rear of the separator insertion portion $50s$. The connector portion $50c$ is crimped to hold a core wire of the sensor output lead 45 for electrical connection between the outer terminal member 50 and the sensor output lead 45.

The outer terminal member 50 is retained in the separator 43 by inserting the separator insertion portion $50s$ in the separator 43 and elastically bringing a separator contact portion $50d$, which branches off and protrudes from the separator insertion portion $50s$, into contact with the retaining hole 43.

The outer engagement portion $50p$ is brought into contact with the outer electrode 23 of the gas sensor element 20 for electrical connection between the outer electrode 23 and the outer terminal member 50.

The inner terminal member 32 is formed of a stainless copper plate and includes an element insertion portion $32k$ having a substantially horseshoe-shaped cross section in the direction perpendicular to the axis AX, a separator insertion portion $32s$ extending toward the rear from the center of a rear end side of the element insertion portion $32k$ and a connector portion $32c$ located rear of the separator insertion portion $32s$. The connector portion $32c$ is crimped to hold a core wire of the sensor output lead 44 for electrical connection between the inner terminal member 32 and the sensor output lead 44.

The inner terminal member 32 is retained in the separator 43 by inserting the separator insertion portion $32s$ in the separator 43 and elastically bringing a separator contact portion $32d$, which branches off and protrudes from the separator insertion portion 32, into contact with the retaining hole $43d$.

The element insertion portion $32k$ of the inner terminal member 32 is inserted in the gas sensor element 20 and brought into contact with the terminal contact portion $21t$ of the inner electrode 21 for electrical connection between the terminal contact portion $21t$ of the inner electrode 21 and the inner terminal member 32.

By the application of a given voltage between the outer electrode 23 and the inner electrode 21, the gas sensor 30 causes a flow of electrical current according to the difference in concentration between the oxygen concentration of the exhaust gas that is brought into contact with the outer sensing portion $23g$ of the outer electrode 23 and the oxygen concentration of the air that is brought into contact with the inner sensing portion $21g$ of the inner electrode 21. The oxygen concentration of the exhaust gas can be determined by detection of this electric current value.

Next, a manufacturing method of the gas sensor 30 of the first embodiment will be described below.

The outer electrode 23 is first formed with the outer sensing portion $23g$, the outer lead portion $23s$ and the outer contact portion $23t$ on the outer surface $1h$ of the base body 1 by a known technique (see, for example, Japanese Laid-Open Patent Publication No. 2007-248123).

Figure 9:
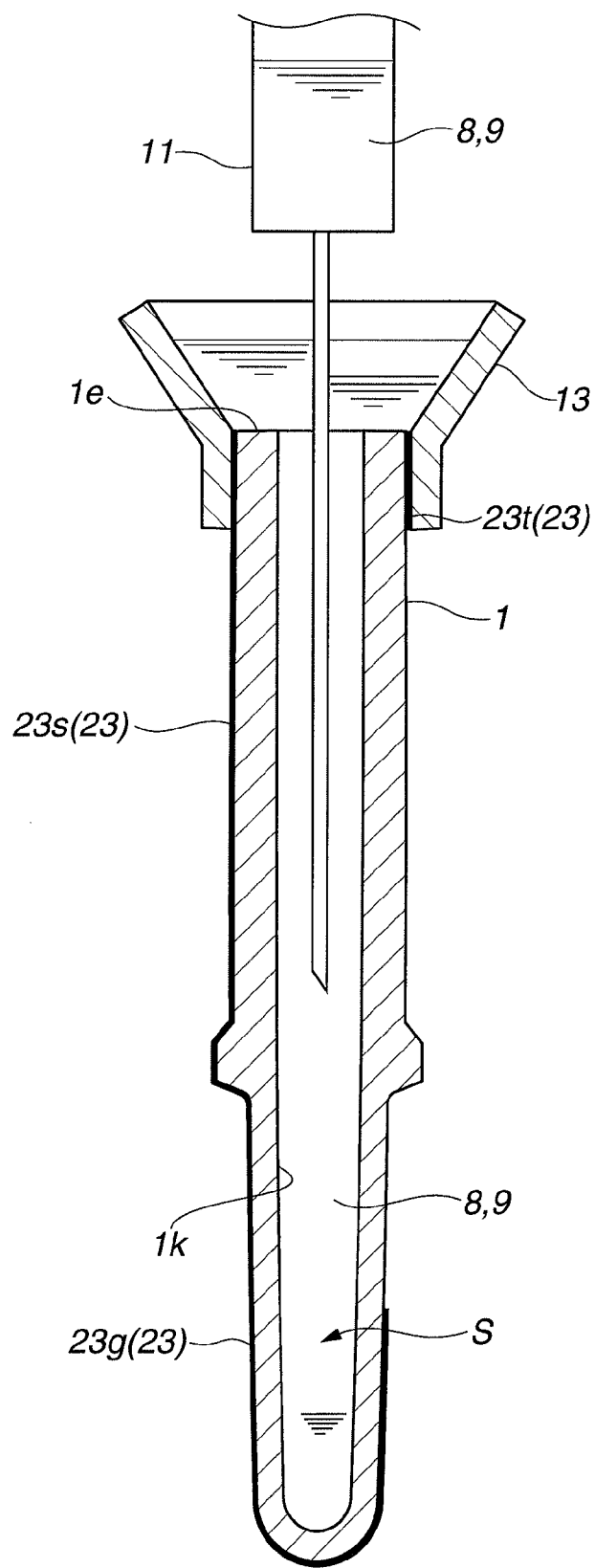
FIG. 9 is a schematic view showing a nucleus application step according to the first to fourth embodiments of the present invention.

The inner electrode 21 is subsequently formed on the inner surface $1k$ of the base body 1. A nucleus application step is first performed to apply nuclei onto the inner surface $1k$ of the base body 1. More specifically, an aqueous platinic chloride solution 8 (platinum concentration: 0.5 g/L) is filled into an inner space S of the base body 1 by means of a liquid filling device 11 as shown in FIG. 9. In the first embodiment, a liquid retaining member 13 of silicon rubber is fitted to the rear end $1e$ of the base body 1 such that the aqueous platinic chloride solution 8 is filled in the inner space S of the base body 1 until it overflows from the inner space S of the base body 1 and reaches the liquid retaining member 13.

The aqueous platinic chloride solution 8 filled in the inner space S of the base body 1 is heated, thereby forming a coating of the aqueous platinic chloride solution on the inner surface $1k$ of the base body 1. After that, the aqueous platinic chloride solution 8 is discharged to the outside from the inner space S of the base body 1 by means of the liquid filling device 11.

An aqueous hydrazine solution 9 (concentration: 5 mass %) is next filled into the inner space S of the base body 1 by means of the liquid filling device 11. In the present embodiment, the aqueous hydrazine solution 9 is also filled in the inner space S of the base body 1 until it overflows from the inner space S of the base body 1 and reaches the liquid retaining member 13. The filled aqueous hydrazine solution 9 is kept heated at 75° C. for 30 minutes. As a result, platinum nuclei are deposited on the inner surface $1k$ of the base body 1. The aqueous hydrazine solution 9 is then discharged to the outside from the inner space S of the base body 1 by means of the liquid filling device 11.

Figure 14:
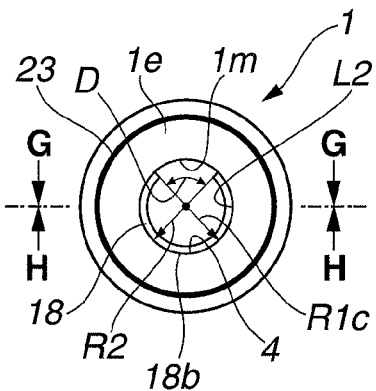
FIG. 14 is a schematic view showing a masking jig attachment step according to the first embodiment of the present invention.
Figure 15:
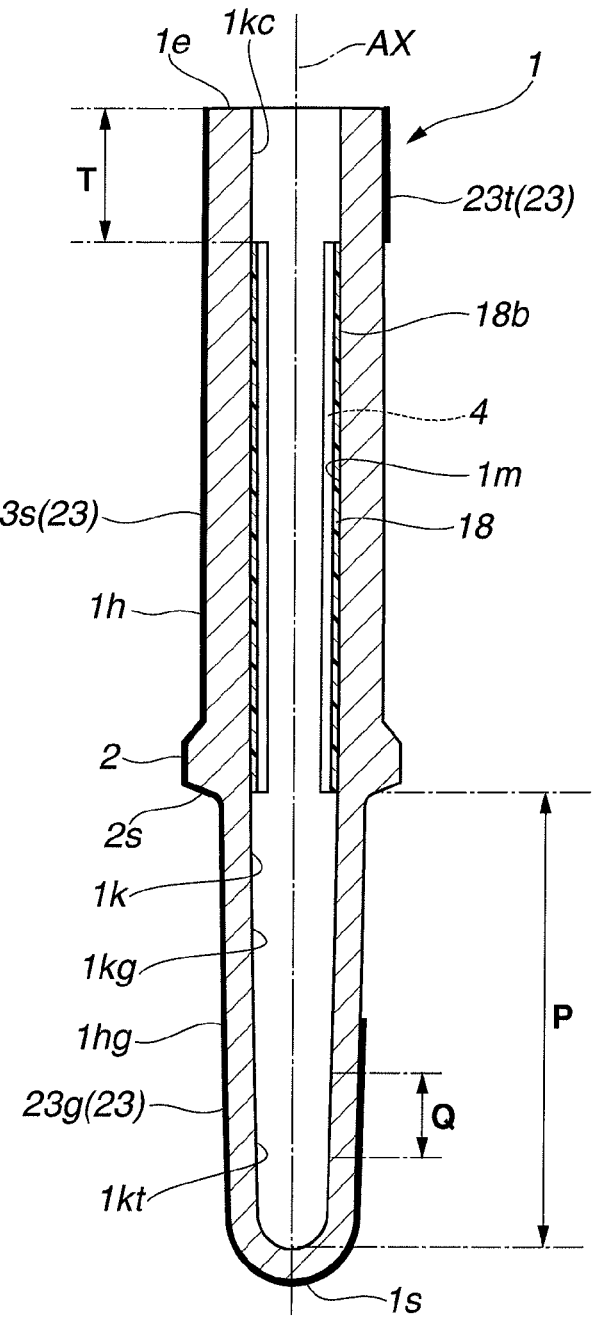
FIG. 15 is a schematic view showing the masking jig attachment step.
Figure 16:
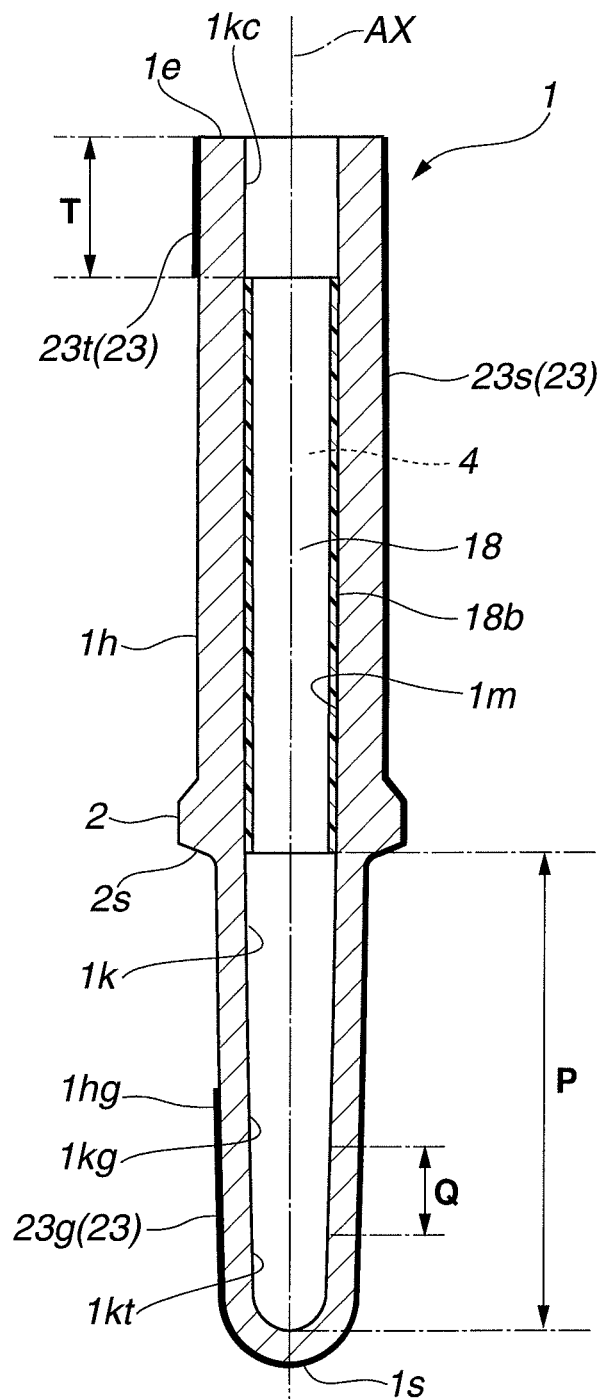
FIG. 16 is a schematic view showing the masking jig attachment step.

Next, a masking jig attachment step is performed to attach a masking jig 18 to a masking region 4 between the gas contact inner region $1kg$ and the rear end region $1kc$ on the inner surface $1k$ of the base body 1 (see FIGS. 14 to 16). The masking region 4 corresponds to any region of the inner surface $1k$ located between the gas contact inner region $1kg$ and the rear end region $1kc$ on the inner surface $1k$ but excluding the circumferential range D (the range of circular arc having a central angle of 80°, on which the lead portion $21s$ is to be formed) (see FIG. 14).

Figure 10:
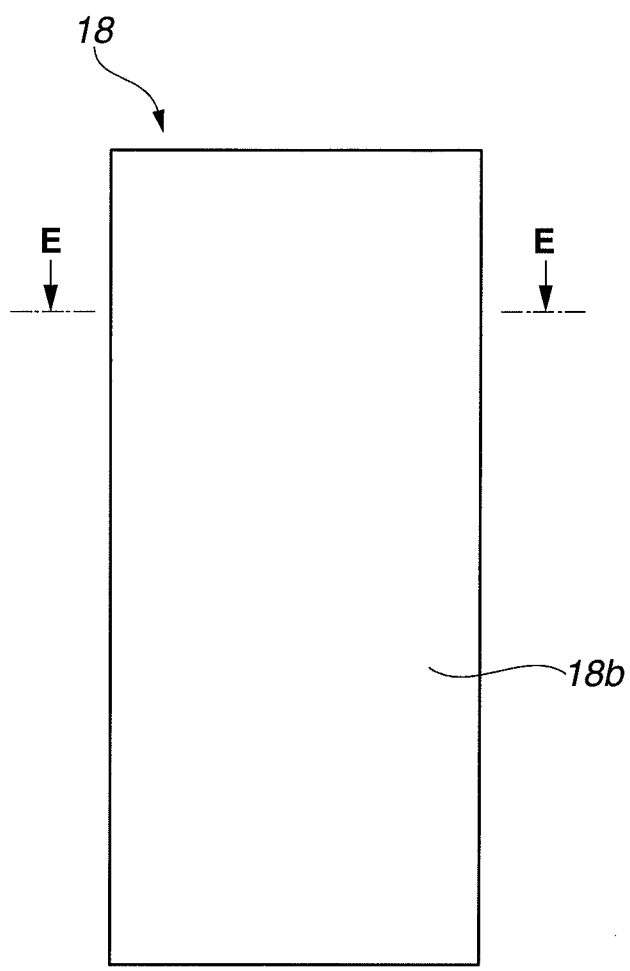
FIG. 10 is a front view of a masking jig according to the first embodiment of the present invention.
Figure 11:
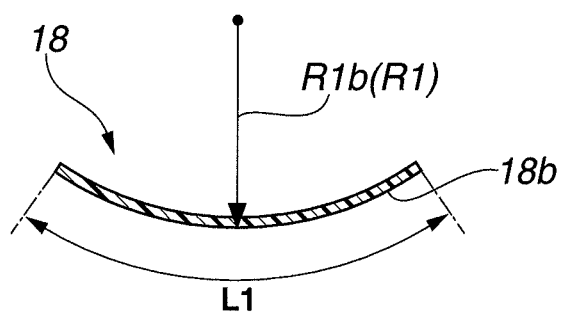
FIG. 11 is a cross-section view of the masking jig taken along arrows E-E in FIG. 10.

The masking jig 18 will be now explained below in detail. The masking jig 18 has a curved plate shaped extending in the axial direction (the direction of the axis AX) (see FIGS. 10 and 11). A masking outer surface 18b is formed on the masking jig 18 such that, when the masking jig 18 is attached to the masking region 4, the masking outer surface 18b comes into contact with the masking region 4. It is herein noted that the vertical direction in FIGS. 10 and 12 agrees with the axial direction (the direction of the axis AX).

In a state that the masking jig 18 is attached to the masking region 4, the masking outer surface 18b forms a circular arc in cross section taken along the direction perpendicular to the direction of the axis AX. A length L1 of this circular arc is larger than half of a circumferential length L2 of a cylindrical part 1m of the inner surface 1k of the base body 1, which includes the masking region 4 in the circumferential direction, and is smaller than the length L2 (see FIGS. 14 and 15). Namely, the condition: (L2/2)<L1<L2 is satisfied. Further, a curvature radius R1 of the masking outer surface 18b before the attachment of the making jig 18 to the making region 4 (the masking outer surface 18b in the state of FIG. 11) is larger than a curvature radius R2 of the making region 4 (see FIG. 14).

Figure 12:
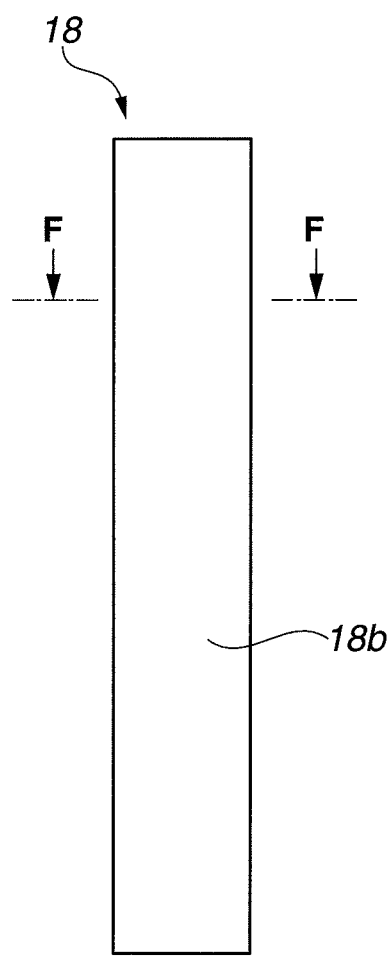
FIG. 12 is a front view of the masking jig (in a state that the masking jig is elastically deformed in a direction that decreases an outer surface curvature radius of the masking jig).
Figure 13:
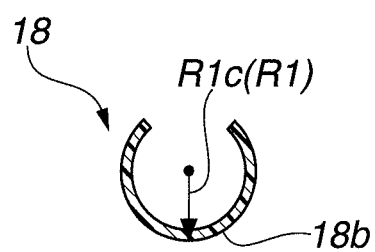
FIG. 13 is a cross-section view of the masking jig (in the state that the masking jig is elastically deformed in the direction that decreases the outer surface curvature radius of the masking jig) taken along arrows F-F in FIG. 10.

The masking jig 18 is made of polypropylene and elastically deformable in a direction that increases or decreases the curvature radius R1 of the masking outer surface 18b. The masking jig 18 can be thus elastically deformed in the direction that decreases the curvature radius R1 of the masking outer surface 18b (e.g. in such a manner that the curvature radius R1 of the masking outer surface 18b is set to the same value R1c as the curvature radius R2 of the making region 4) as shown in FIGS. 12 and 13.

In the making jig attachment step, the masking jig 18 is fixed to the making region 4 by inserting the masking jig 18 into the base body 1 (to a position that overlaps the making region 4) while elastically deforming the masking jig 18 in the direction that decreases the curvature radius R1 of the masking outer surface 18b (i.e. controlling the curvature radius R1 of the masking outer surface 18b to be smaller than or equal to the curvature radius R2 of the making region 4) (see FIGS. 14 to 16), and then, brining the masking outer surface 18b into contact with the making region 4 under elastic restoring force of the masking jig 18 (whereby the curvature radius of the masking outer surface 18b takes the same value R1c as the curvature radius R2 of the making region 4, see FIG. 14). In this way, the masking jig attachment step is performed to attach the masking jig 18 to the making region 4 of the inner surface 1k of the base body 1 (i.e. to cover the making region 4 with the masking jig 18) in the first embodiment.

It is noted that: FIG. 14 is a top view of the base body 1 (i.e. a view of the base body 1 as viewed from the side of the rear end 1e of the base body 1) in the state that the masking jig 18 is attached to the base body 1; FIG. 15 is a cross-section view of the base body 1 taken along arrows H-H in FIG. 14; and FIG. 16 is a cross-section view of the base body 1 taken along arrows G-G in FIG. 14.

Figure 17:
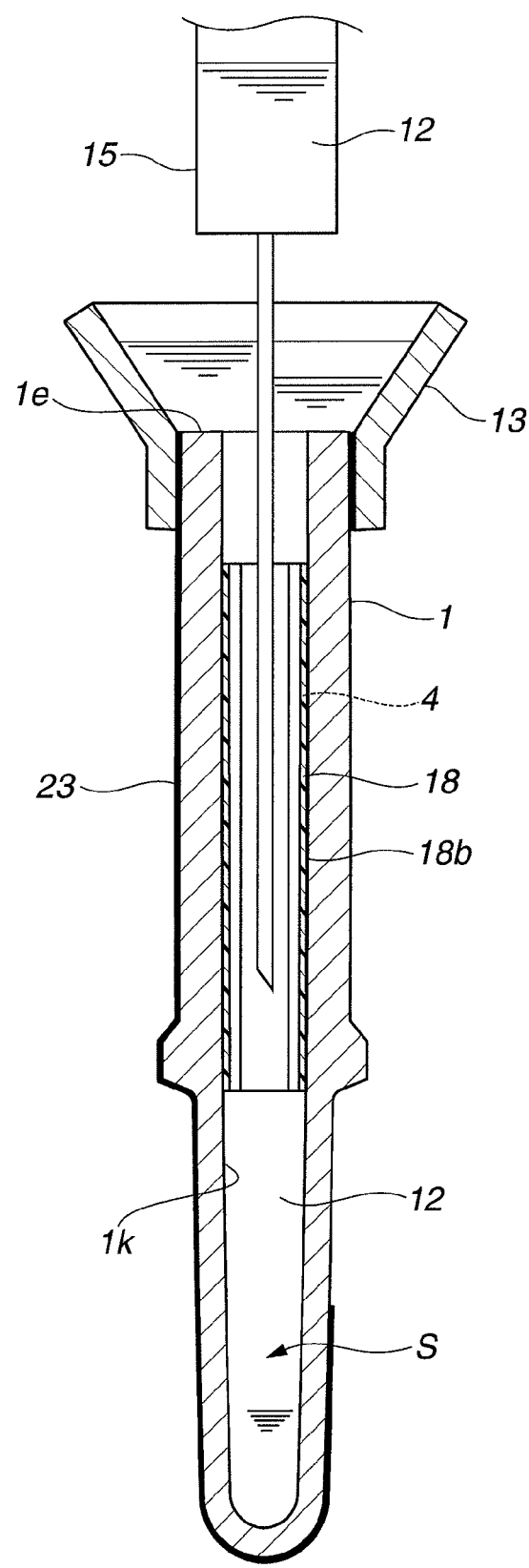
FIG. 17 is a schematic view showing a plating step according to the first embodiment of the present invention.

A plating step is subsequently performed with the use of a plating liquid 12, on which the nuclei deposited on the inner surface 1k of the base body 1 act as a catalyst, to deposit noble metal (platinum) out of the plating liquid 12 to the inner surface 1k of the base body 1 (any region of the inner surface 1k other than the making region 4 on which the masking jig 18 is present). More specifically, the plating liquid 12 is filled into the inner space S of the base body 1 by means of a liquid filling device 15 as shown in FIG. 17. In a state that the liquid retaining member 13 is fitted to the rear end 1e of the base body 1, the plating liquid is filled until it overflows from the inner space S of the base body 1 and reaches the liquid retaining member 13. In the first embodiment, the plating liquid 12 is prepared by mixing an aqueous platinum complex salt solution (platinum concentration: 15 g/L) with an aqueous hydrazine solution (concentration: 85 mass %).

The plating liquid 12 filled in the inner space S of the base body 1 is heated and left for a predetermined time. With this, the platinum is deposited out of the plating liquid 12 to the inner surface 1k of the base body 1 (the region of the inner surface 1k other than the making region 4 on which the masking jig 18 is present). The plating liquid 12 is then discharged to the outside from the inner space S of the base body 1 by means of the liquid filling device 15.

In the first embodiment, the masking jig attachment step in which the masking jig 18 is attached to the making region 4 of the inner surface 1k of the base body 1 (the making region 4 is covered with the masking jig 18) is performed prior to the plating step as mentioned above. This makes it possible to deposit the noble metal (platinum) only on the part of the inner surface 1k of the base body 1 on which the masking jig 18 is not present, without causing deposit of the noble metal (platinum) to the part of the inner surface 1k of the base body 1 on which the masking jig 18 is present (the making region 4).

Figure 18:
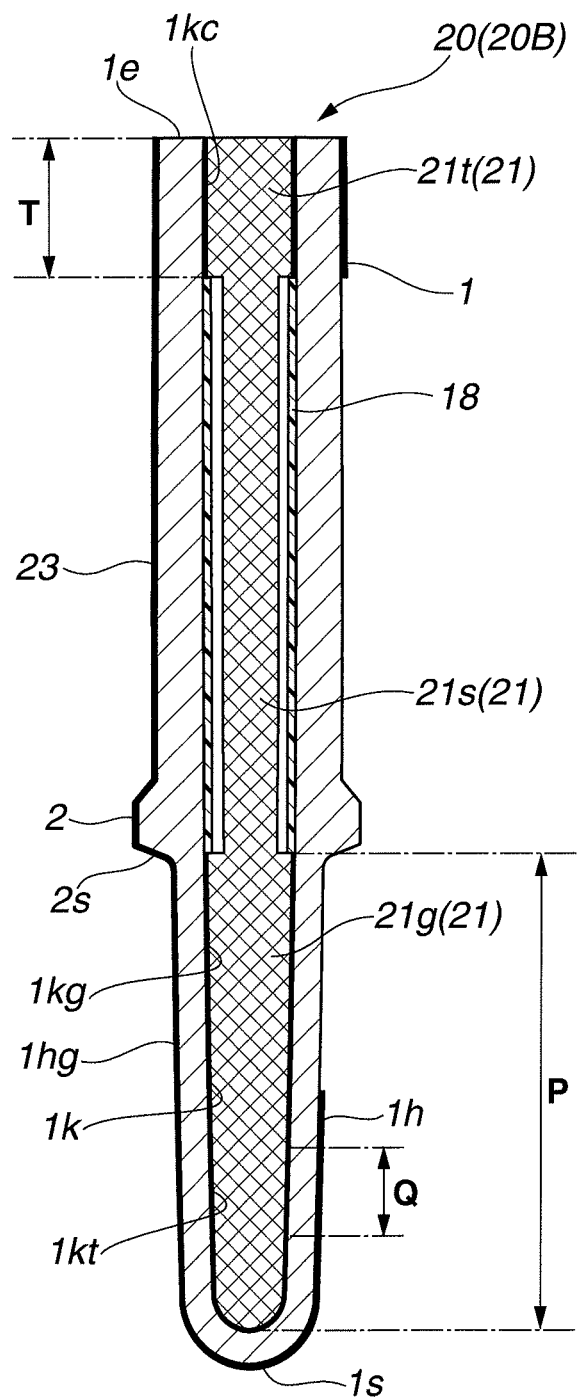
FIG. 18 is a schematic view showing the plating step.
Figure 19:
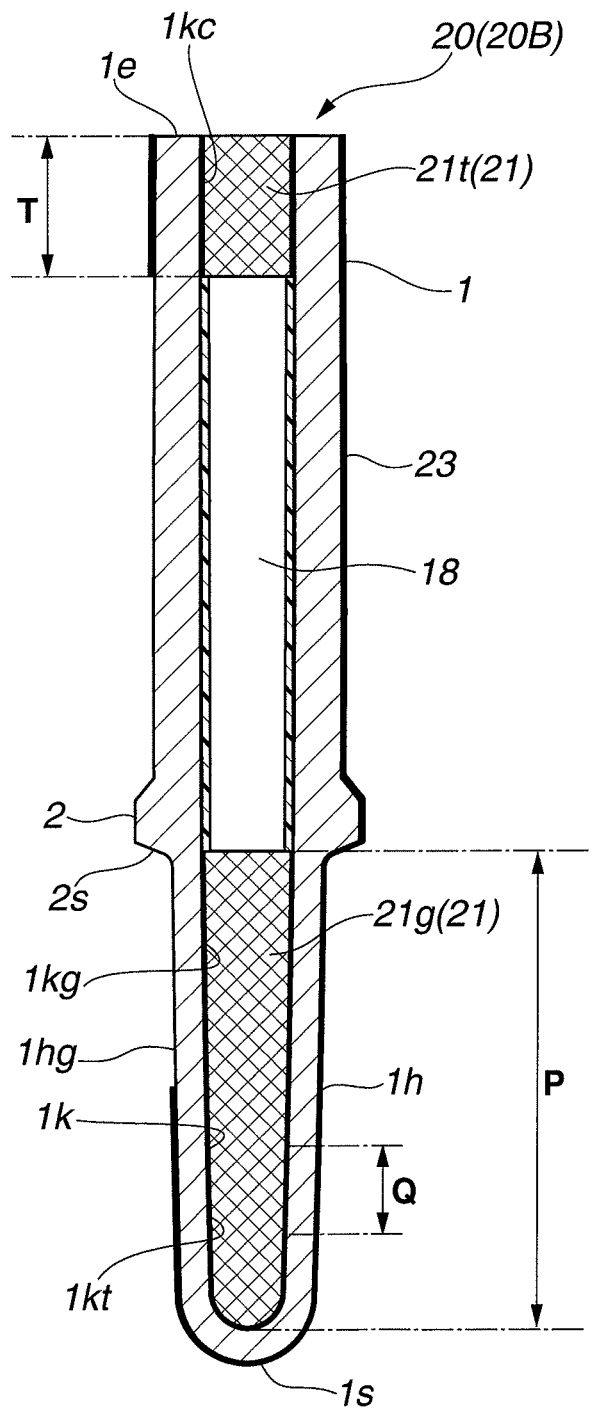
FIG. 19 is a schematic view showing the plating step.

As a result, the inner electrode 21 of noble metal (platinum) (as a noble metal plating layer) is formed only on the part of the inner surface 1k of the base body 1 on which the masking jig 18 is not present as shown in FIGS. 18 and 19. More specifically, the inner sensing portion 21g is formed on the whole of the gas contact inner region 1kg including the heat-facing area 1kt; the inner contact portion 21t is formed on the whole of the rear end region 1kc; and the inner lead portion 21s is formed only on the part of the inner surface 1k in the circumferential direction of the base body 1 (i.e. in the circumferential range D) so as to extend linearly in the axial direction (the direction of the axis AX) for connection between the inner sensing region 21g and the inner contact portion 21t.

It is noted that: FIG. 18 is a cross-section view of the plated base body 20B (i.e. the base body 1 having the noble metal deposited on the inner surface 1k thereof) taken at the same position as in FIG. 15; and FIG. 19 is a cross-section view of the plated base body 20B taken at the same position as in FIG. 16.

As described above, the inner electrode 21 (the inner sensing portion 21g, the inner lead portion 21s and the inner contact portion 21t) can be formed selectively on the part of the inner surface 1k of the base body 1 where the electrode is required by the manufacturing method of the first embodiment. It is thus possible in the first embodiment to reduce the amount of the noble metal used as compared to the case of forming a noble metal electrode by deposition of noble metal on the whole of an inner surface of a base body in a plating step.

The masking jig 18 is then detached from the plated base body 20B (see FIGS. 6 and 7). As the masking jig 18 is fixed to the making region 4 only by its elastic restoring force, it is possible to easily detach the masking jig 18 from the plated base body 20B.

After that, a reduction treatment step is performed to heat treat the plated base body 20B in a reducing atmosphere of 750° C. In this reduction treatment step, the inner electrode 21 is formed with specific characteristics by removing oxygen adsorbed on the surface of the inner electrode 21 (noble metal plating layer) and baking the inner electrode 21 (noble metal plating layer) onto the inner surface 1k of the base body 1. The gas sensor element 20 of the first embodiment is herewith completed (see FIGS. 6 and 7). Using the above-produced gas sensor element 20, the gas sensor 30 of FIG. 1 is manufactured by a known assembling process (see, for example, Japanese Laid-Open Patent Publication No. 2004-053425).

[Second Embodiment]

A second embodiment of the present invention will be described below with reference to the drawings.

A gas sensor 130 of the second embodiment (see FIG. 1) is structurally similar to the gas sensor 30 of the first embodiment, except for the shapes of outer and inner electrodes (more specifically, inner sensing portion and lead portion). Thus, differences of the second embodiment from the first embodiment will be mainly described below; and the descriptions of the same parts or portions of the second embodiment as those of the first embodiment will be omitted or simplified.

The gas sensor 130 of the second embodiment includes a gas sensor element 120 (see FIG. 1). The gas sensor element 120 has the same base body 1 as that of the first embodiment, an outer electrode 123 formed of noble metal (more specifically, platinum) on the outer surface 1h of the base body 1 and an inner electrode 121 formed of noble metal (more specifically, platinum) (as a noble metal plating layer) on the inner surface 1k of the base body 1 (see FIGS. 20 to 22).

Figure 20:
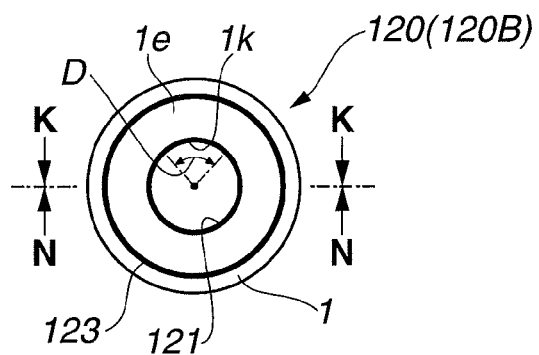
FIG. 20 is a top view of a gas sensor element according to the second embodiment of the present invention.
Figure 21:
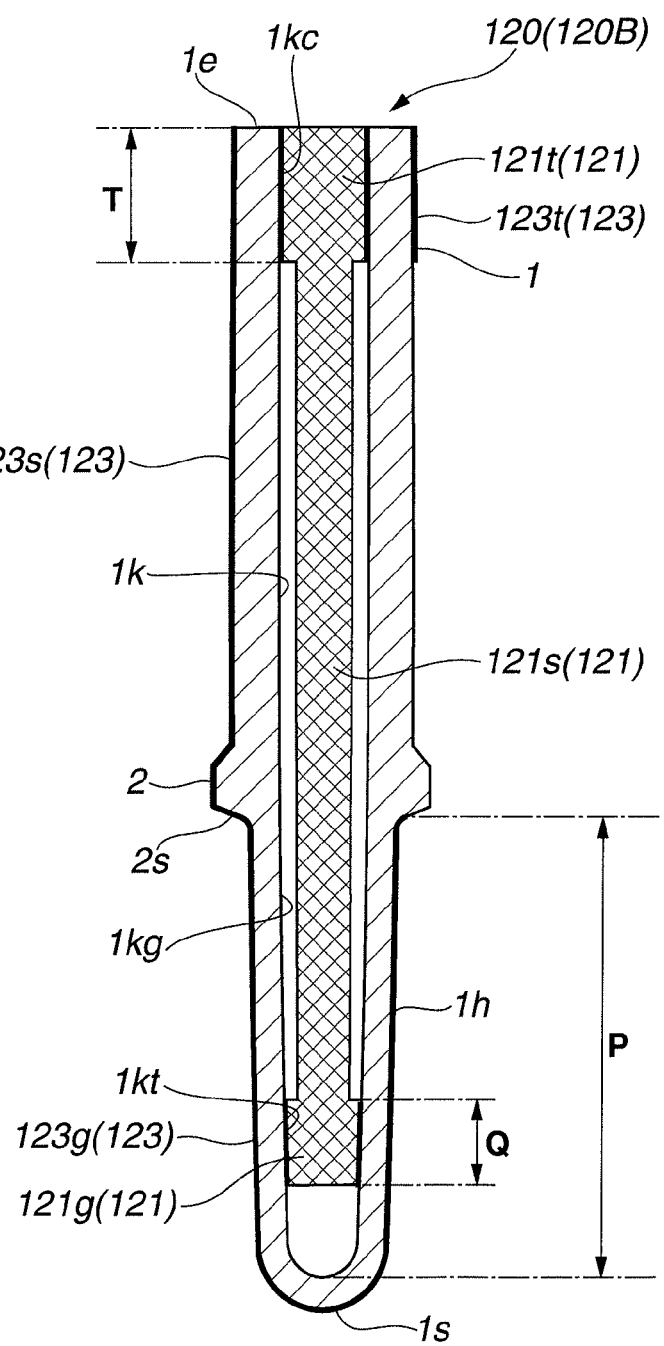
FIG. 21 is a vertical cross-section view of the gas sensor element taken along arrows N-N in FIG. 20.

It is noted that: FIG. 20 is a top view of the gas sensor element 120 (a view of the gas sensor element 120 as viewed from the side of the rear end 1e of the base body 1 in the direction of the axis AX); FIG. 21 is a cross-section view of the gas sensor element 120 taken along arrows N-N in FIG. 20; and FIG. 22 is a cross-section view of the gas sensor element 120 taken along arrows K-K in FIG. 20.

Figure 22:
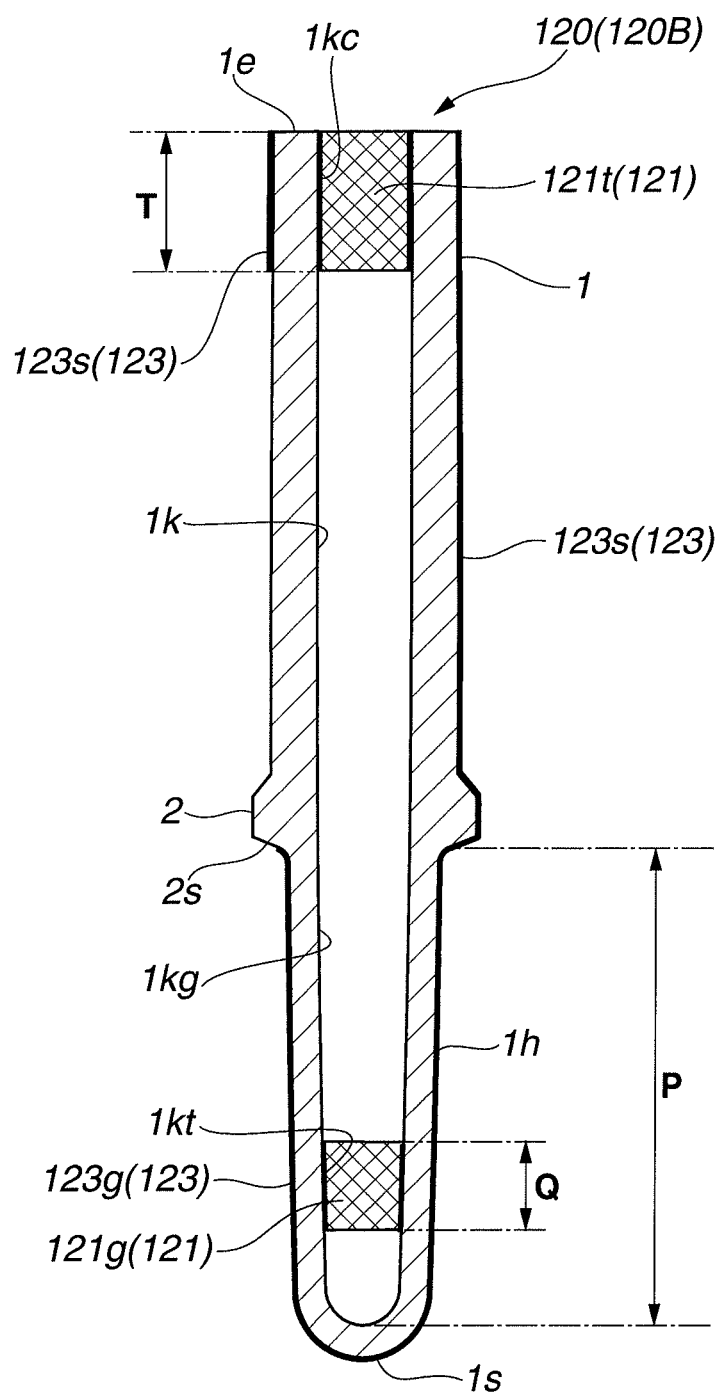
FIG. 22 is a vertical cross-section view of the gas sensor element taken along arrows K-K in FIG. 20.

As shown in FIGS. 21 and 22, the inner electrode 121 has an inner sensing portion 121g formed in the gas contact inner region 1kg (the region within the axial range P), an inner contact portion 121t formed in the rear end region 1kc (the region within the axial range T) and an inner lead portion 121s connecting the gas contact inner region 1kg and the inner contact portion 121t to each other. The inner contact portion 121t is located on the whole (entire circumference) of the rear end region 1kc as in the case of the inner contact portion 21t of the first embodiment.

The inner sensing portion 121g is located only on the heat-facing area 1kt of the gas contact inner region 1kg (i.e. the area within the axial range Q). It is thus possible to further reduce the amount of the noble metal used in the gas sensor 130 of the second embodiment, as compared with the gas sensor 30 of the first embodiment where the inner sensing portion 21g is located on the whole of the gas contact inner region 1kg. It is also possible that the gas sensor 130 can obtain a stable sensor output quickly upon energization of the heater 33 as the inner sensing portion 121g is formed on the heat-facing area 1kt.

Further, the inner lead portion 121s is formed only on the part of the inner surface 1k in the circumferential direction of the base body 1. More specifically, the inner lead portion 121s is formed only on the circumferential range D (the range of circular arc having a central angle of 80°, see FIG. 20) in such a manner as to extend linearly in the axial direction (the direction of the axis AX) as in the case of the inner lead portion 21s of the first embodiment. Herein, the inner lead portion 121s of the second embodiment is made longer than the inner lead portion 21s of the first embodiment. More specifically, the inner lead portion 121s of the second embodiment is in the form that the inner lead portion 21s of the first embodiment is extended toward the front end 1s (to a position rear of the heat-facing area 1kt).

The outer electrode 123 has an outer sensing portion 123g formed in the gas contact region 1hg (see FIGS. 21 and 22).

The outer sensing portion 123g is located on at least an area of the gas contact region 1hg inside of which the inner sensing portion 121g is located in the thickness direction of the base body 1. As is different from the first embodiment, the outer sensing portion 123g is formed on the whole of the gas contact region 1hg in the second embodiment. The outer electrode 123 also has an outer lead portion 123s and an outer contact portion 123t formed on the outer surface of the base body 1 such that the outer lead portion 123s connects to the outer sensing portion 123g and extends linearly in the axial direction and such that the outer contact portion 123t connects to the outer lead portion 123s.

A manufacturing method of the gas sensor 130 of the second embodiment will be described below. First, the outer electrode 123 is formed on the outer surface 1h of the base body 1 in the same manner as in the first embodiment. A nucleus application step is next performed in the same manner as in the first embodiment, thereby applying nuclei to the inner surface 1k of the base body 1 (see FIG. 9).

Figure 23:
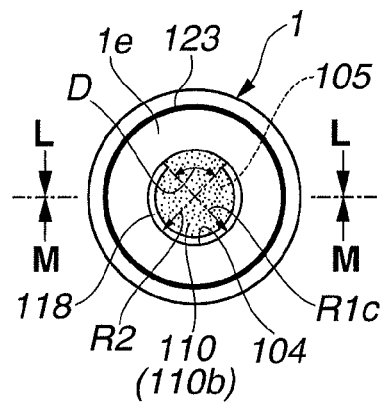
FIG. 23 is a schematic view showing a plating resist film formation step and a masking jig attachment step according to the second embodiment of the present invention.
Figure 24:
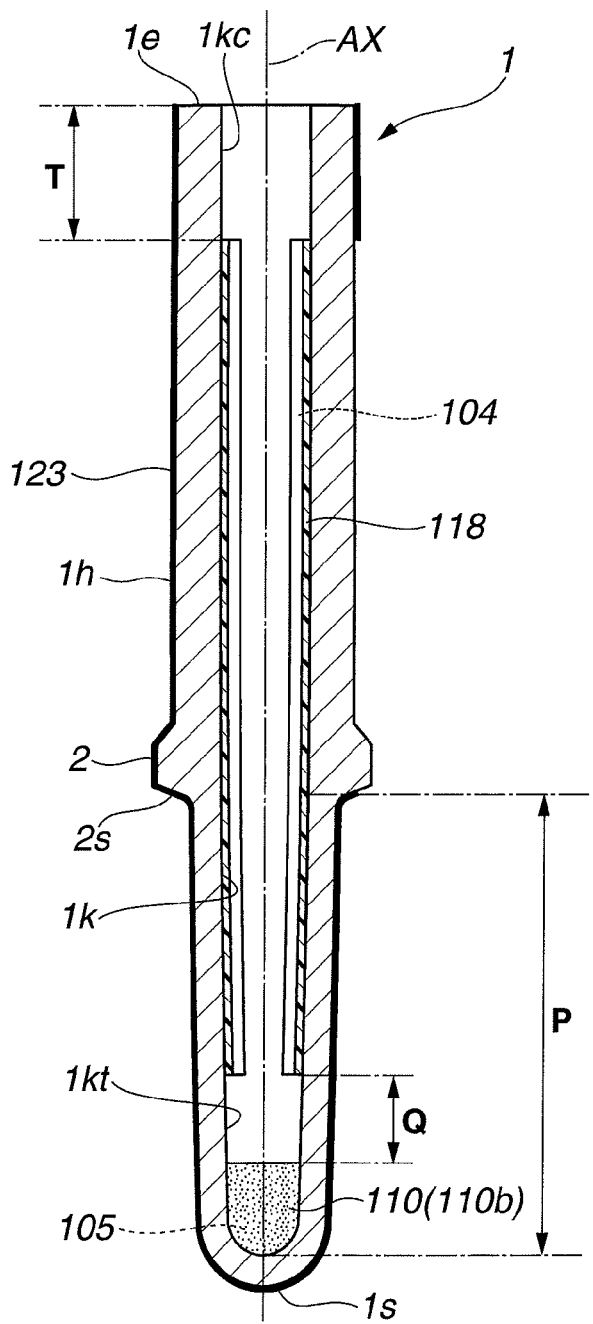
FIG. 24 is a schematic view showing the plating resist film formation step and the masking jig attachment step.
Figure 25:
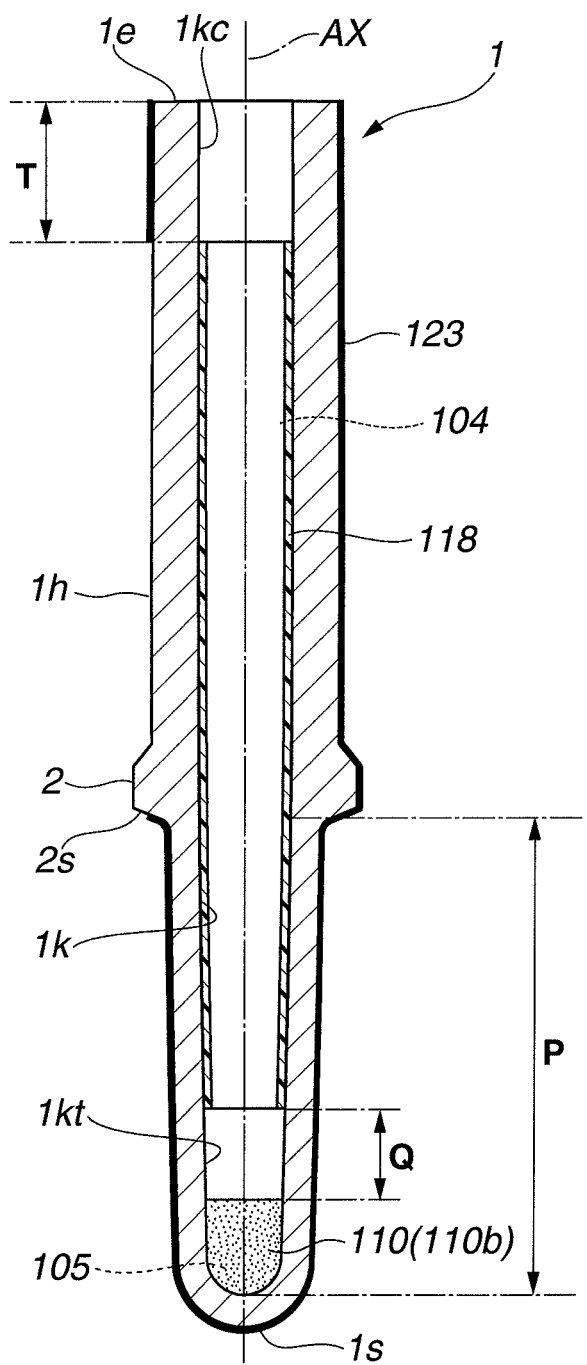
FIG. 25 is a schematic view showing the plating resist film formation step and the masking jig attachment step.

A plating resist film formation step is then performed to form a plating resist film 110 on the whole of any region of the inner surface 1k of the base body 1 located closer to the front end 1s than the heat-facing area 1kt (see FIGS. 23 to 25). (This region is hereinafter referred to as "plating resist region 105".) More specifically, the plating resist film 110 is formed by applying a plating resist 110b to the plating resist region 105 and hardening the applied plating resist 110b by heat drying. In the second embodiment, an acrylic emulsion "Saibinol CA-1108" (as a trade name, available from Saiden Chemical Industry Co., Ltd.) is used as the plating resist 110b. This plating resist 110b is a plating resist (coating) of organic substance containing no metal component. The resulting plating resist film 110 is thus of organic substance containing no metal component.

A masking jig attachment step is subsequently performed in the same manner as in the first embodiment, to attach a masking jig 118 to a making region 104 between the heat-facing area 1kt and the rear end region 1kc on the inner surface 1k of the base body 1 (see FIGS. 23 to 25). The making region 104 corresponds to any region of the inner surface 1k located between the heat-facing area 1kt and the rear end region 1kc on the inner surface 1k but excluding the circumferential range D (the range of circular arc having a central angle of 80° on which the lead portion 21s is to be formed).

It is noted that: FIG. 23 is a top view of the base body 1 (a view of the base body 1 as viewed from the side of the rear end 1e of the base body 1 in the direction of the axis AX) in a state that the masking jig 18 is attached; FIG. 24 is a cross-section view of the base body 1 taken along arrows M-M in FIG. 23; and FIG. 25 is a cross-section view of the base body 1 taken along arrows L-L in FIG. 23.

The masking jig 118 of the second embodiment is different from the masking jig 18 of the first embodiment, in that the masking jig 118 is elongated in the axial direction (the direction of the axis AX). In the second embodiment, a length of the masking jig 118 in the axial direction is set so as to extend from a rear end of the heat-facing area 1kt (top end in FIG. 24, top end of the axial range Q) to a front end of the rear end region 1kc (bottom end in FIG. 24, bottom end of the axial range T).

Next, a plating step is performed in the same manner as in the first embodiment, to deposit noble metal (platinum) out of a plating liquid 12 to the inner surface 1k of the base body 1. In the second embodiment, the plating resist film 110 is formed on the plating resist region 105 and the masking jig 118 is attached to the making region 104 prior to the plating step as mentioned above.

In this plating step, the noble metal (platinum) can be thus deposited to the part of the inner surface 1k of the base body 1 on which the masking jig 118 and the plating resist film 110 are not present, without causing deposit of the noble metal (platinum) to the part (masking region 104 and plating resist region 105) of the inner surface 1k of the base body 1 on which the masking jig 118 and the plating resist film 110 are present.

Figure 26:
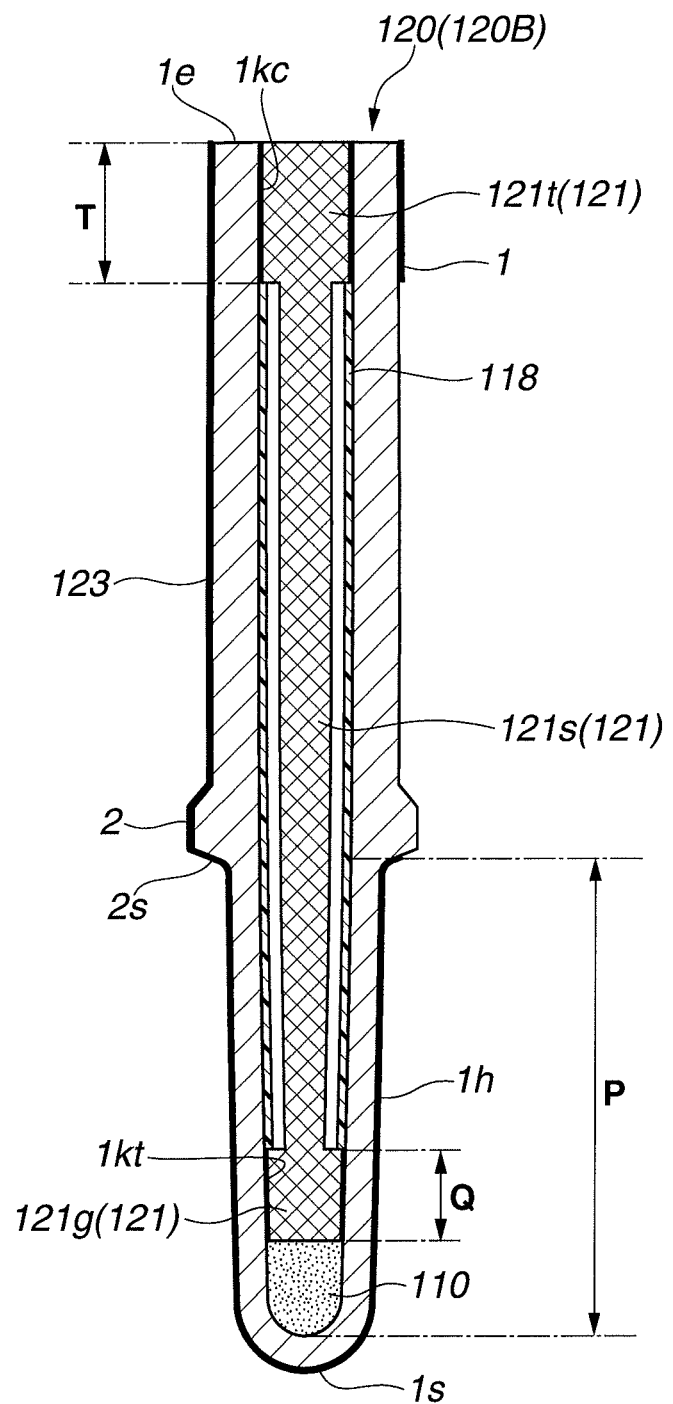
FIG. 26 is a schematic view showing a plating step according to the second embodiment of the present invention.
Figure 27:
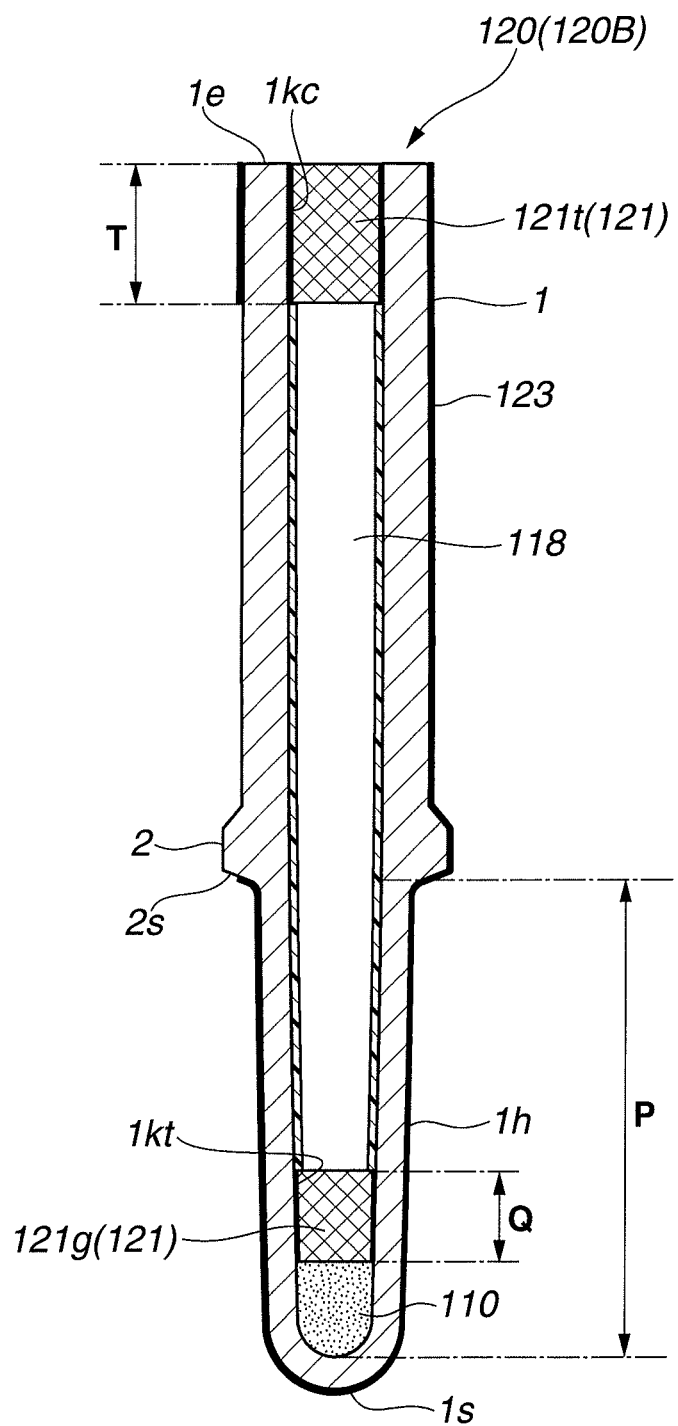
FIG. 27 is a schematic view showing the plating step.

As a result, the inner electrode 121 of noble metal (platinum) (as a noble metal plating layer) is formed only on the part of the inner surface 1k of the base body 1 on which the masking jig 118 and the plating resist film 110 are not present as shown in FIGS. 26 and 27. More specifically, the inner sensing portion 121g is formed only on the heat-facing area 1kt; the inner contact portion 121t is formed on the whole of the rear end region 1kc; and the inner lead portion 121s is formed only on the part of the inner surface 1k in the circumferential direction of the base body 1 (circumferential range D) so as to extend linearly in the axial direction (the direction of the axis AX) for connection between the inner sensing region 121g and the inner contact portion 121t.

It is noted that FIG. 26 is a cross-section view of the plated base body 120B (i.e. the base body 1 having the noble metal deposited on the inner surface 1k thereof) taken at the same position as in FIG. 24; and FIG. 27 is a cross-section view of the plated base body 120B taken at the same position as in FIG. 25.

The masking jig 118 is detached from the plated base body 120B in the same manner as in the first embodiment. A burning step is then performed. In the burning step, the plated base body 120B from which the making jig 118 has been detached is subjected to heat treatment at about 500° C. in the air so as to burn off the plating resist film 110. With this, the plating resist film 110 can be removed appropriately from the inner surface 1k (plating resist region 105) of the base body 1 (see FIGS. 21 and 22). As compared to the case of removing the plating resist film by peeling, it is possible to easily and appropriately remove the plating resist film by burning off the plating resist film.

If a metal component is contained in the plating resist film, there is a possibility that the metal component remains on the inner surface of the base body after the burn-off of the plating resist film in the burning step. The performance characteristics of the gas sensor may be affected by such a remaining metal component. For this reason, it is unfavorable that the metal component is contained in the plating resist film.

In the second embodiment, the plating resist film 110 is formed of organic substance containing no metal component in the plating resist film formation step as mentioned above. Thus, there does not occur the above problem that the metal component remains on the inner surface of the base body (the region on which the plating resist film has been formed). It is possible to appropriately burn off the plating resist film 110 of organic substance.

After that, a reduction treatment step is performed. In the reduction treatment step, the plated base body 20B from which the plating resist film 110 has been burned off is subjected to heat treatment in a reducing atmosphere of 750° C. The inner electrode 121 is then formed with specific characteristics by removing oxygen adsorbed on the surface of the inner electrode 121 (noble metal plating layer) and baking the inner electrode 121 (noble metal plating layer) onto the inner surface 1k of the base body 1. The gas sensor element 120 of the second embodiment is herewith completed (see FIGS. 20 to 22).

There is a possibility that the characteristics of the electrode 121 (noble metal plating layer) may be affected (the specific characteristics of the electrode 121 may not be obtained) when, in the burning step, the plated base body 120B is exposed to a temperature environment higher than or close to the heating temperature (750° C.) of the reduction treatment step. In the burning step of the second embodiment, the plating resist film 110 is burned off at a temperature of 700° C. or lower (more specifically, about 500° C.), which is lower than the heating temperature of the reduction treatment step. In other words, the plating resist film 111 is formed in the plating resist film formation step such that the plating resist film 111 can be burned off at 700° C. or lower (the burning temperature of the plating resist film 111 is 700° C. or lower) (more specifically, about 500° C.), which is lower than the heating temperature of the reduction treatment step. There is thus no fear of the above problem (that the characteristics of the electrode 121 are affected in the burning step).

Using the above-produced gas sensor element 120, the gas sensor 130 of the second embodiment (see FIG. 1) is manufactured by a known assembling process (see, for example, Japanese Laid-Open Patent Publication No. 2004-053425).

[Third Embodiment]

A third embodiment of the present invention will be described below with reference to the drawings.

A gas sensor 230 of the third embodiment (see FIG. 1) is structurally similar to the gas sensor 30 of the first embodiment, except for the shapes of outer and inner electrodes (more specifically, terminal contact portion). Thus, differences of the third embodiment from the first embodiment will be mainly described below; and the descriptions of the same parts or portions of the third embodiment as those of the first embodiment will be omitted or simplified.

The gas sensor 230 of the third embodiment includes a gas sensor element 220 (see FIG. 1). The gas sensor element 220 has the same base body 1 as that of the first embodiment, an outer electrode 223 formed of noble metal (more specifically, platinum) on the outer surface 1h of the base body 1 and an inner electrode 221 formed of noble metal (more specifically, platinum) (as a noble metal plating layer) on the inner surface 1k of the base body 1 (see FIGS. 28 to 30).

Figure 28:
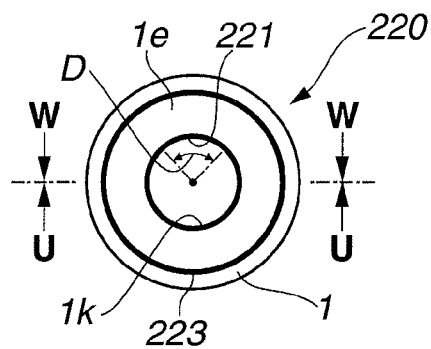
FIG. 28 is a top view of a gas sensor element according to the third embodiment of the present invention.
Figure 29:
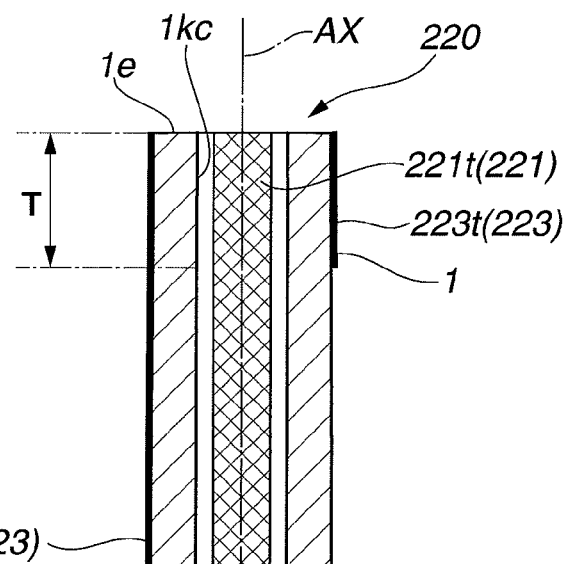
FIG. 29 is a vertical cross-section view of the gas sensor element taken along arrows U-U in FIG. 28.
Figure 29:
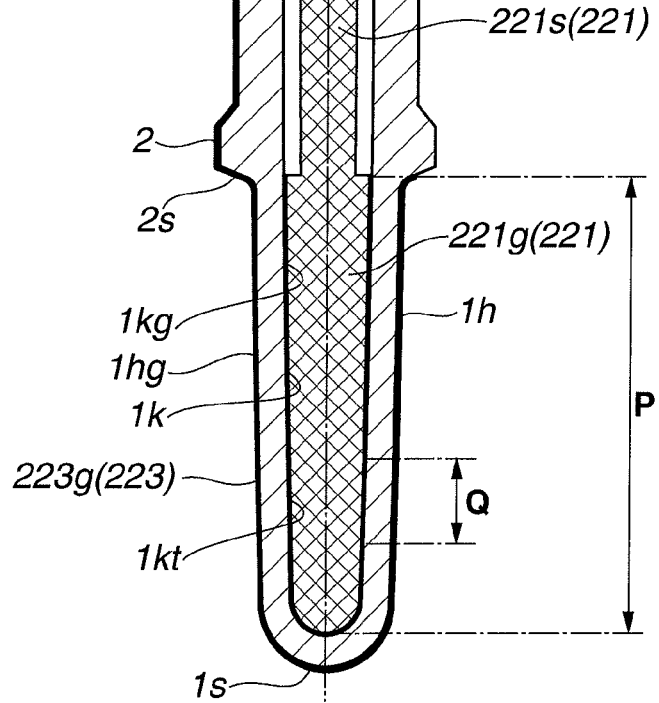

It is noted that: FIG. 28 is a top view of the gas sensor element 220 (a view of the gas sensor element 220 as viewed from the side of the rear end 1e of the base body 1 in the direction of the axis AX); FIG. 29 is a cross-section view of the gas sensor element 220 taken along arrows U-U in FIG. 28; and FIG. 30 is a cross-section view of the gas sensor element 220 taken along arrows W-W in FIG. 28.

Figure 30:
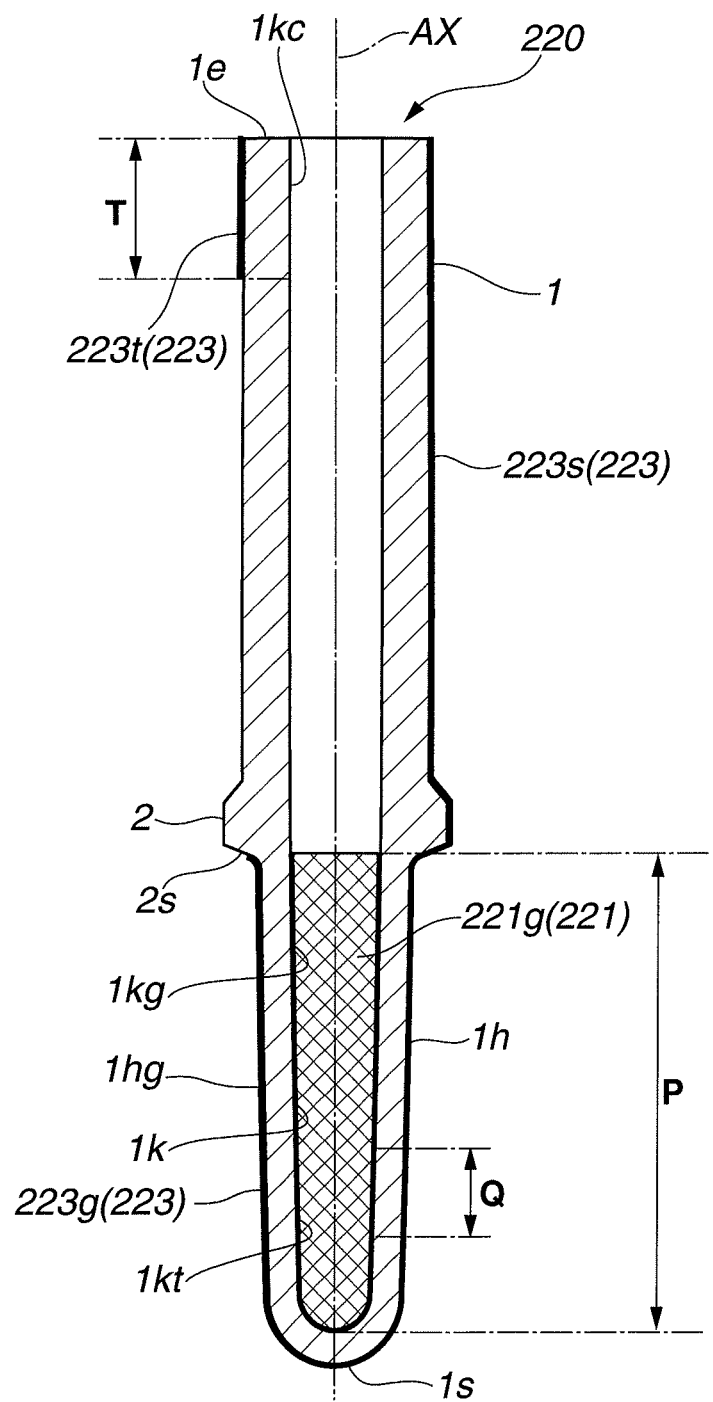
FIG. 30 is a vertical cross-section view of the gas sensor element taken along arrows W-W in FIG. 28.

As shown in FIGS. 29 and 30, the inner electrode 221 has an inner sensing portion 221g formed in the gas contact inner region 1kg (the region within the axial range P), an inner contact portion 221t formed in the rear end region 1kc (the region within the axial range T) and an inner lead portion 221s connecting the inner sensing portion 221g and the inner contact portion 221t to each other.

The inner sensing portion 221g is located on the whole of the gas contact inner region 1kg as in the case of the inner sensing portion 21g of the first embodiment. The inner lead portion 221s is also located in the same range as the inner lead portion 21s of the first embodiment. More specifically, the inner lead portion 221s is formed only in the circumferential range D (the range of circular arc having a central angle of 80°, see FIG. 28) in such a manner as to extend linearly in the axial direction (the direction of the axis AX) from a rear end of the gas contact inner region 1kg (top end in FIG. 29) to a front end of the rear end region 1kc (bottom end in FIG. 29).

On the other hand, the inner contact portion 221t is located only a part of the rear end region 1kc in the circumferential direction of the base body 1 as is different from the inner contact portion 21t of the first embodiment. More specifically, the inner contact portion 221t of the third embodiment is formed only in the circumferential range D (the range of circular arc having a central angle of 80°, see FIG. 28) as in the case of the inner lead portion 221s.

It is possible to further reduce the amount of the noble metal (platinum) used on the inner surface 1k of the base body 1 by forming the inner contact portion 221t only on the part of the inner surface 1k (rear end region 1kc) in the circumferential direction of the base body 1 rather than by forming the inner contact portion 221t on the whole (entire circumference) of the inner surface 1k (rear end region 1kc) in the circumferential direction of the base body 1.

The outer electrode 223 has an outer sensing portion 223g formed in the gas contact region 1hg (see FIGS. 29 and 30). The outer sensing portion 223g is located on at least an area of the gas contact region 1hg inside of which the inner sensing portion 221g is located in the thickness direction of the base body 1. As is different from the first embodiment, the outer sensing portion 223g is formed on the whole of the gas contact region 1hg. The outer electrode 223 also has an outer lead portion 223s and an outer contact portion 223t formed on the outer surface of the base body 1 such that the outer lead portion 223s connects to the outer sensing portion 223g and extends linearly in the axial direction and such that the outer contact portion 223t connects to the outer lead portion 223s.

The inner contact portion 221t can be formed by e.g. the following procedure. In the third embodiment, provided is a masking jig that is elongated in the axial direction by a length of the rear end region 1kc (a length of the axial range T) as compared with the masking jig 18 of Example 1. The masking jig is placed on a part of the inner surface 1k of the base body 1 from a rear end of the gas contact inner region 1kg (top end in FIG. 29) to the rear end 1e of the base body 1. In this state, a plating step is performed, whereby the inner contact portion 221t can be formed together with the inner sensing portion 221g and the lead portion 221s.

[Fourth Embodiment]

A fourth embodiment of the present invention will be described below with reference to the drawings.

A gas sensor 330 of the fourth embodiment (see FIG. 1) is structurally similar to the gas sensor 30 of the first embodiment, except for the shape of an inner electrode (more specifically, inner sensing portion). Thus, differences of the fourth embodiment from the first embodiment will be mainly described below; and the descriptions of the same parts or portions of the fourth embodiment as those of the first embodiment will be omitted or simplified.

The gas sensor 330 of the fourth embodiment includes a gas sensor element 320 (see FIG. 1). The gas sensor element 320 has the same base body 1 as that of the first embodiment, the same outer electrode 23 as that of the first embodiment and an inner electrode 321 formed of noble metal (more specifically, platinum) (as a noble metal plating layer) on the inner surface 1k of the base body 1 (see FIGS. 31 to 33).

Figure 31:
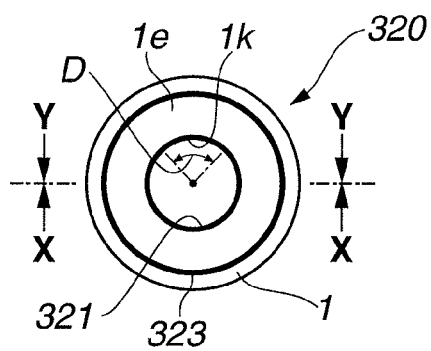
FIG. 31 is a top view of a gas sensor element according to the fourth embodiment of the present invention.
Figure 32:
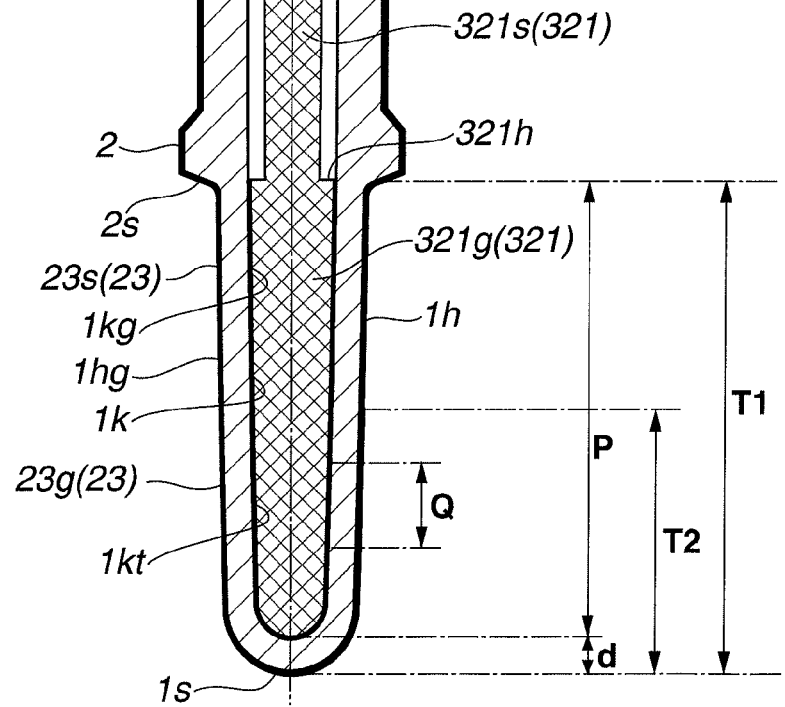
FIG. 32 is a vertical cross-section view of the gas sensor element taken along arrows X-X in FIG. 31.

It is noted that: FIG. 31 is a top view of the gas sensor element 320 (a view of the gas sensor element 320 as viewed from the side of the rear end 1e of the base body 1 in the direction of the axis AX); FIG. 32 is a cross-section view of the gas sensor element 320 taken along arrows X-X in FIG. 31; and FIG. 33 is a cross-section view of the gas sensor element 320 taken along arrows Y-Y in FIG. 31.

Figure 33:
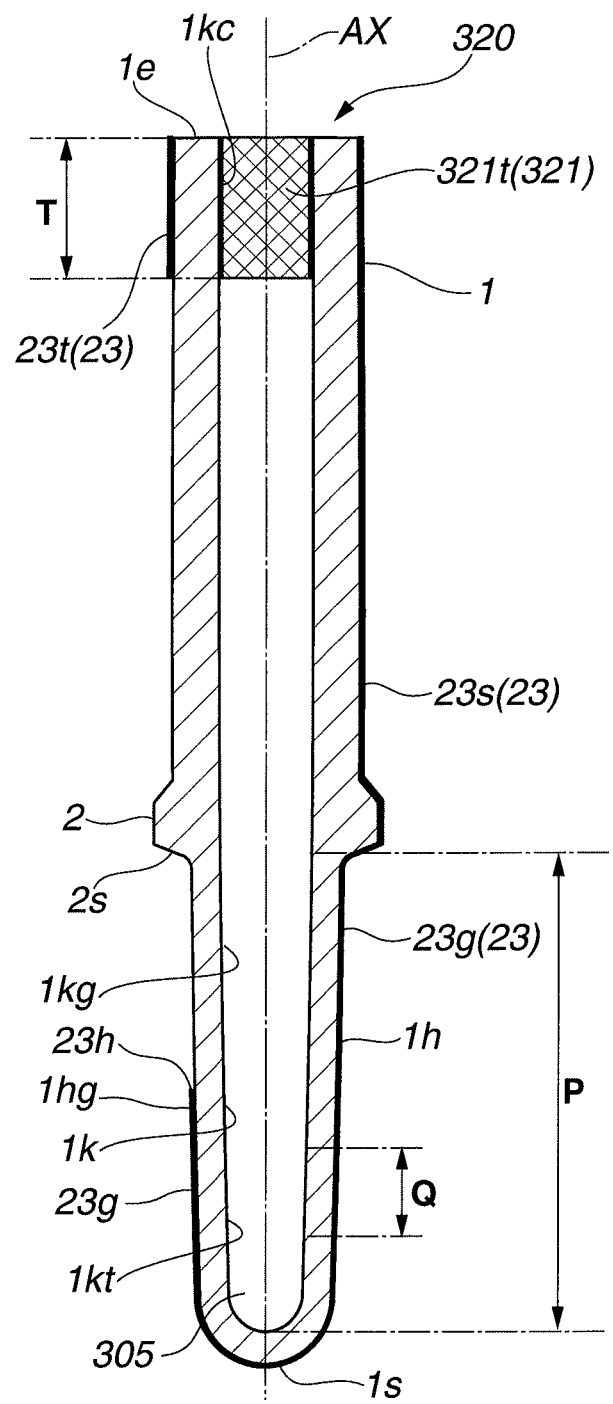
FIG. 33 is a vertical cross-section view of the gas sensor element taken along arrows Y-Y in FIG. 31.

As shown in FIGS. 32 and 33, the inner electrode 321 has an inner sensing portion 321g formed in the gas contact inner region 1kg (the region within the axial range P), an inner contact portion 321t formed in the rear end region 1kc (the region within the axial range T) and an inner lead portion 321s connecting the inner sensing portion 321g and the inner contact portion 321t to each other.

The inner contact portion 321t is located on the whole (entire circumference) of the rear end region 1kc as in the case of the inner contact portion 21t of the first embodiment. The inner lead portion 321s is also located in the same range as the inner lead portion 21s of the first embodiment. More specifically, the inner lead portion 321s is formed only in the circumferential range D (the range of circular arc having a central angle of 80°, see FIG. 31) in such a manner as to extend linearly in the axial direction (the direction of the axis AX) from a front end of the rear end region 1kc (bottom end in FIG. 32) to a rear end of the gas contact inner region 1kg (top end in FIG. 32).

On the other hand, the inner sensing portion 321g is located only a part of the gas contact inner region 1kg in the circumferential direction of the base body 1 as is different from the inner sensing portion 21g of the first embodiment. More specifically, the inner sensing portion 321g of the fourth embodiment is formed only on a half part (half circumference) of the gas contact inner region 1kg in the circumferential direction of the base body 1 (see FIGS. 32 and 33).

It is possible to further reduce the amount of the noble metal (platinum) used on the inner surface 1k of the base body 1 by forming the inner sensing portion 321g only on the part of the inner surface 1k in the circumferential direction of the base body 1 rather than by forming the inner sensing portion 321g on the whole (entire circumference) of the inner surface 1k in the circumferential direction of the base body 1.

In the gas sensor 330 of the fourth embodiment, the heater 33 is in contact with the inner sensing portion 321g (see FIG. 1). When the inner sensing portion 321g is formed only on the part of the gas contact inner region 1kg (in the fourth embodiment, the half circumferential part of the gas contact inner region 1kg) in the circumferential direction of the base body 1 and selectively brought into contact with the heater 33, the part of the base body 1 on which the inner sensing portion 321g is formed is easier to heat and can be activated more rapidly. It is thus possible to obtain a stable sensor output more quickly upon energization of the heater 33.

The inner sensing portion 321g can be formed by e.g. the following procedure. Prior to a plating step, the same plating resist 110b as that of Example 2 is applied to the half part (half circumference) of the gas contact inner region 1kg in the circumferential direction of the base body 1 (plating resist region 305, see FIG. 33). The applied plating resist 110b is hardened by heat drying, thereby forming a plating resist film. Further, a masking jig 18 is attached in the same manner as in the first embodiment. In this state, the plating step is performed, whereby the inner sensing portion 321g can be formed together with the inner contact portion 321t and the inner lead portion 321s.

Although the present invention has been described above with reference to the first to fourth embodiments, the present invention is not limited to these exemplary embodiments. It is needless to say that various modifications and variations of the embodiments described above can be made without departing from the scope of the present invention.

DESCRIPTION OF REFERENCE NUMERALS

1: Base body
1s: Front end of base body
1e: Rear end of base body
1h: Outer surface of base body
1k: Inner surface of base body
1hg: Gas contact region 1*kg*: Gas contact inner region
1*kc*: Rear end region
1*kt*: Heat-facing area
18, 118: Masking jig
20, 120, 220, 320: Gas sensor element
21, 121, 221, 321: Inner electrode
21*g*, 121*g*, 221*g*, 321*g*: Inner sensing portion
21*s*, 121*s*, 221*s*, 321*s*: Lead portion
21*t*, 121*t*, 221*t*, 321*t*: Terminal contact portion
23, 123, 223: Outer electrode
23*g*, 123*g*, 223*g*: Outer sensing portion
23*s*, 123*s*, 223*s*: Lead portion
23*t*, 123*t*, 223*t*: Terminal contact portion
30, 130, 230, 330: Gas sensor
33: Heater
33*c*: Heating portion

The invention claimed is:

1. A gas sensor, comprising:
a gas sensor element for detecting a specific gas component in gas under measurement, the gas sensor element including: a bottomed cylindrical base body formed of a solid electrolyte with a closed front end and an open rear end and extending in an axial direction of the gas sensor; an outer electrode formed of noble metal on an outer surface of the base body; and an inner electrode formed of noble metal on an inner surface of the base body; and
a heater having a heating portion arranged in a cylindrical inner space of the base body,
wherein the outer surface of the base body includes a gas contact region located on a front end side of the base body such that the gas under measurement comes into contact with the gas contact region;
wherein the inner surface of the base body includes a gas contact inner region at a position located inside of the gas contact region in a thickness direction of the base body and a rear end region spaced apart from the gas contact inner region in the axial direction and located at a rear end side of the base body;
wherein the heating portion has a heating resistor pattern located only in the same axial range as that where the gas contact inner region is located in the axial direction;
wherein the inner electrode has: an inner sensing portion formed only in the gas contact inner region such that the inner sensing portion is located on at least the whole of a heat-facing area of the gas contact inner region that faces the heating resistor pattern in a radial direction of the base body; a terminal contact portion formed in the rear end region such that the terminal contact portion is located on at least a part of the rear end region in a circumferential direction of the base body; and a lead portion formed only on a part of the inner surface in the circumferential direction of the base body so as to connect the inner sensing portion and the terminal contact portion to each other;
wherein the outer electrode has an outer sensing portion formed in the gas contact region such that a part of the outer sensing portion is located on at least a part of the gas contact region inside of which the inner sensing portion is located in the thickness direction of the base body;
wherein a rear end of the inner sensing portion is located rear of a rear end of the outer sensing portion; and
wherein the following condition: $1.1 < T1/T2$ is satisfied where $T1$ is a length between a front end of the gas sensor element and the rear end of the inner sensing portion in the axial direction; and $T2$ is a length between the front end of the gas sensor element and the rear end of the outer sensing portion in the axial direction.

2. The gas sensor according to claim 1, wherein the inner sensing portion is formed only on the heat-facing area.

3. The gas sensor according to claim 1, wherein the inner sensing portion is formed only on a part of the gas contact inner region in the circumferential direction of the base body.

4. The gas sensor according to claim 1, wherein the lead portion extends linearly in the axial direction.

5. The gas sensor according to claim 1, wherein the heater is in contact with the inner sensing portion.

6. The gas sensor according to claim 1, wherein a thickness of the outer sensing portion is larger than a thickness of the inner sensing portion.

7. The gas sensor according to claim 1, wherein the heat-facing area is located on the inner surface of a part of the base body having a thickness of d to 2d where d is a minimum thickness of the base body.

8. The gas sensor according to claim 1, wherein the heat-facing area is located on the inner surface of a part of the base body that reaches 70% or higher of a maximum heating temperature of the gas sensor element.

* * * * *